United States Patent
Mavunkel et al.

(10) Patent No.: US 6,340,685 B1
(45) Date of Patent: Jan. 22, 2002

(54) COMPOUNDS AND METHODS TO TREAT CARDIAC FAILURE AND OTHER DISORDERS

(75) Inventors: Babu J. Mavunkel, Sunnyvale; John A. Lewicki, Los Gatos; David Y. Liu, Palo Alto; George F. Schreiner, Los Altos Hills; John J. Perumattam, Los Altos, all of CA (US)

(73) Assignee: Scios, Inc., Sunnyvale, CA (US)

( * ) Notice: Subject to any disclaimer, the term of this patent is extended or adjusted under 35 U.S.C. 154(b) by 0 days.

(21) Appl. No.: 09/275,176

(22) Filed: Mar. 24, 1999

Related U.S. Application Data

(63) Continuation-in-part of application No. 09/128,137, filed on Aug. 3, 1998, now Pat. No. 6,130,235.

(60) Provisional application No. 60/086,531, filed on May 22, 1998.

(51) Int. Cl.$^7$ .................... A61K 31/496; C07D 403/06
(52) U.S. Cl. .................. 514/253; 544/367; 544/370; 544/373
(58) Field of Search .................. 514/253; 544/367, 544/370, 373

(56) References Cited

U.S. PATENT DOCUMENTS 4,088,765 A    5/1978    Winn et al. .................. 514/307

(List continued on next page.)

FOREIGN PATENT DOCUMENTS

EP    0 318 235    5/1989

(List continued on next page.)

OTHER PUBLICATIONS

Gassman, P. G., "A General Method for the Synthesis of Indoles," J. Am. Chem. Soc., (1974) 96(17): 5495–5508.

(List continued on next page.)

Primary Examiner—Ceila Chang
(74) Attorney, Agent, or Firm—Morrison & Foerster LLP

(57) ABSTRACT

A compound of the formula:

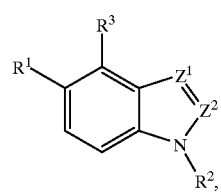

(1)

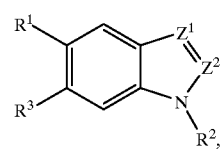

(2)

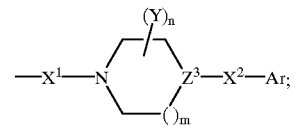

(3)

(4)

and the pharmaceutically acceptable salts thereof, wherein each of $Z^1$ and $Z^2$ is independently $CR^4$ or N;

where each $R^4$ is independently H or is alkyl (1–6C) optionally including one or more heteroatoms selected from O, S and N and optionally substituted by one or more of halo, OR, SR, $NR_2$, RCO, COOR, $CONR_2$, OOCR, or NROCR where R is H or alkyl (1–6C), or by CN or =O, or by an aliphatic or aromatic 5 or 6 membered ring optionally containing 1–2 N heteroatoms; or two $R^4$ taken together form a bridge optionally containing a heteroatom;

$R^1$ is $$-X^1-N \overbrace{\underset{()_m}{\underbrace{(Y)_n}}} Z^3-X^2-Ar;$$

wherein
$X^1$ is CO or an isostere thereof;
m is 0 or 1;
Y is optionally substituted alkyl, optionally substituted aryl, or optionally substituted arylalkyl or two 6 taken together may form an alkyene (2–3C) bridge;
n is 0 or 2;
$Z^3$ is CH or N;
$X^2$ is CH, $CH_2$ or an isostere thereof; and
Ar consists of one or two phenyl moieties directly coupled to $X^2$ optionally substituted by halo, nitro, alkyl (1–6C), alkenyl (1–6C), CN or $CF_3$, or by RCO, COOR, $CONR_2$, $NR_2$, OR, SR, OOCR or NROCR wherein R is H or alkyl (1–6C) or by phenyl, itself optionally substituted by the foregoing substituents;
$R^2$ is H, or alkyl (1–6C) optionally including one heteroatom which is O, S or N, and optionally substituted by one or more of halo, OR, SR, $NR_2$, RCO, COOR, $CONR_2$, OOCR, or NROCR where R is H or alkyl (1–6C), or by CN or =O, or by an aliphatic or aromatic 5 or 6 membered ring optionally containing 1–2 N heteroatoms;
$R^3$ is H, halo, $NO_2$, alkyl (1–6C), alkenyl (1–6C), CN, OR, SR, $NR_2$, RCO, COOR, $CONR_2$, OOCR, or NROCR where R is H or alkyl (1–6C).

12 Claims, No Drawings

U.S. PATENT DOCUMENTS

| | | | | |
|---|---|---|---|---|
| 4,243,806 A | | 1/1981 | Raeymaekers et al. | 544/396 |
| 4,454,130 A | * | 6/1984 | Tominaga et al. | 546/158 |
| 5,462,934 A | | 10/1995 | Goto et al. | 514/183 |
| 5,698,553 A | | 12/1997 | Prucher et al. | 514/222.8 |
| 5,714,498 A | | 2/1998 | Kulagowski et al. | 514/307 |
| 5,726,177 A | * | 3/1998 | Halazy et al. | 514/253 |
| 5,795,907 A | * | 8/1998 | Kalindjian et al. | 514/397 |

FOREIGN PATENT DOCUMENTS

| | | | |
|---|---|---|---|
| EP | | 0 431 945 | 6/1991 |
| EP | | 0 709 384 | 5/1996 |
| EP | | 0 831 090 | 3/1998 |
| JP | | 2-184673 | 7/1990 |
| JP | | 3-161470 | * 7/1991 |
| WO | WO 96/40143 | | 12/1996 |
| WO | WO 97/26252 | | 7/1997 |
| WO | WO 98/06715 | | 2/1998 |
| WO | WO 98/07425 | | 2/1998 |
| WO | WO 98/28292 | | 7/1998 |

OTHER PUBLICATIONS

Murai, Y., et al., "*Synthesis of 4–, 5–, 6– and 7–Substituted N–Tosylindoles from Substituted Anilines,* " Heterocycles, (1992) 34(5):1017–1029.

Li, Z. et al. "The primary structure of p38γ: a new member of p38 group of MAP kinases" *Biochem Biophys Res Comm* (1996) 228:334–340.

Stein, B. et al. "p38–2, a novel mitogen–activated protein kinase with distinct properties", *J Biol Chem* (1997) 272:19509–19517.

Wang, X.S., et al., "Molecular cloning and characterization of a novel p38 mitogen–activated protein kinase", *J Biol Chem* (1997) 272:23668–23674.

Wang, Y. et al. "Cardiac muscle cell hypertrophy and apoptosis induced by distinct members of the p38 mitogen–activated protein kinase family", *J Biol Chem* (1998) 273:2161–2168.

Eyers, P.A. et al. "Conversion of SB 203580–insensitive MAP kinase family members to drug–sensitive forms by a single amino–acid substitution", *Chem and Biol* (1995) 5:321–328.

Fischer, "Physical chemical properties and local anesthetic results of an ether substitute of procaine"CA 67:10051 (1996).

International Search Report dated Jul. 29, 1999.

Jiang, Y. et al., "Characterization of the structure and function of a new mitogen–activated protein kinase (p38β)" *J Biol Chem* (1996) 271:17920–17926.

Kumar, S. et al. "Novel homologues of CSBP/p38 MAP kinase: activation, substrate specificity and sensitivity to inhibition by pyridinyl imidazoles", *Biochem Biophys Res Comm* (1997) 235:533–538.

Otsuka Pharm. "Carbostyril derivatives" CA 100:51465, 1983.*

Otsuka Pharm. "Carbostyril derivatives" CA 100:34414, 1983.*

Otsuka Pharm. "Carbostyril derivatives as cardiotonics" CA 100:68187, 1984.*

Nakai et al. "Carbostyril derivatives for . . . " CA 121:222012, 1994.*

Fischer "Physical–chemical properties and local . . . " CA 67:10051, 1966.*

Oelschlaeger et al. "Synthesis of new compounds with local anestetic . . . " CA 109:73387, 1988.*

De Clerck et al. "Effect of flunarizine . . . " CA 96:97376, 1981.*

Von Strandtmann "4–substituted4–methylsulfinylmethylcarbostyrils" CA 80:82713, 1971.*

Schmit et al. "Histamine increases anti–CD#. . . " CA 122:53913, 1994.*

Nakai et al. "Carbostyril derivatives for . . . " CA 121:221997, 1994.*

* cited by examiner

COMPOUNDS AND METHODS TO TREAT CARDIAC FAILURE AND OTHER DISORDERS

This application is a continuation in part of U.S. Ser. No. 09/128,137, now U.S. Pat. No. 6,130,235, filed Aug. 3, 1998 which application claims priority under 35 U.S.C. 119(e) of provisional application No. 60/086,531 filed May 22, 1998. The contents of these applications are incorporated herein by reference.

TECHNICAL FIELD

The invention is directed to compounds that are useful in treating inflammation and that contain piperazine or piperidine moieties coupled to the 5-or 6-position of indole, benzimidazole or benzotriazole. More particularly, the invention concerns novel ortho substituted indoles and N-substituted indoles as well as methods to treat heart and kidney conditions using these compounds and derivatives thereof.

BACKGROUND ART

A large number of chronic and acute conditions have been recognized to be associated with perturbation of the inflammatory response. A large number of cytokines participate in this response, including IL-1, IL-6, IL-8 and TNF. It appears that the activity of these cytokines in the regulation of inflammation rely at least in part on the activation of an enzyme on the cell signaling pathway, a member of the MAP kinase family generally known as p38 and alternatively known as CSBP and RK. This kinase is activated by dual phosphorylation after stimulation by physiochemical stress, treatment with lipopolysaccharides or with proinflammatory cytokines such as IL-1 and TNF. Therefore, inhibitors of the kinase activity of p38 are useful antiinflammatory agents.

PCT applications WO98/28292, WO98/06715, WO98/07425, and WO96/40143, all of which are incorporated herein by reference, describe the relationship of p38 kinase inhibitors with various disease states. As mentioned in these applications, inhibitors of p38 kinase are useful in treating a variety of diseases associated with chronic inflammation. These applications list rheumatoid arthritis, rheumatoid spondylitis, osteoarthritis, gouty arthritis and other arthritic conditions, sepsis, septic shock, endotoxic shock, Gram-negative sepsis, toxic shock syndrome, asthma, adult respiratory distress syndrome, stroke, reperfusion injury, CNS injuries such as neural trauma and ischemia, psoriasis, restenosis, cerebral malaria, chronic pulmonary inflammatory disease, silicosis, pulmonary sarcosis, bone resorption diseases such as osteoporosis, graft-versus-host reaction, Crohn's Disease, ulcerative colitis including inflammatory bowel disease (IBD) and pyresis.

The above-referenced PCT applications disclose compounds which are p38 kinase inhibitors said to be useful in treating these disease states. These compounds are either imidazoles or are indoles substituted at the 3- or 4-position with a piperazine or piperidine ring linked through a carboxamide linkage. Additional compounds which are conjugates of piperazines with indoles are described as insecticides in WO97/26252, also incorporated herein by reference.

DISCLOSURE OF THE INVENTION

The invention is directed to compounds useful in treating inflammation generally, including specific conditions such as those described in the Background section above. Certain novel compounds have been found to inhibit p38 kinase, in particular, p38 kinase α and are thus useful in treating diseases mediated by this enzyme. The compounds of the invention are of the formula

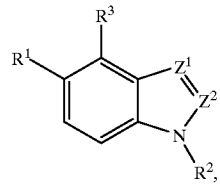
(1)

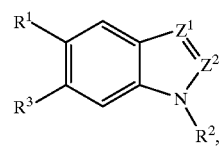
(2)

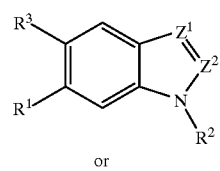
(3)

or

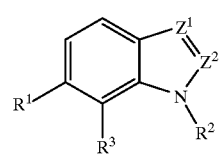
(4)

and the pharmaceutically acceptable salts thereof,
wherein each of $Z^1$ and $Z^2$ is independently $CR^4$ or N;
where each $R^4$ is independently H or is alkyl (1–6C) optionally including one or more heteroatoms selected from O, S and N and optionally substituted by one or more of halo, OR, SR, $NR_2$, RCO, COOR, $CONR_2$, OOCR, or NROCR where R is H or alkyl (1–6C), or by CN or =O, or by an aliphatic or aromatic 5 or 6 membered ring optionally containing 1–2 N heteroatoms; or
two $R^4$ taken together form a bridge optionally containing a heteroatom;
$R^1$ is

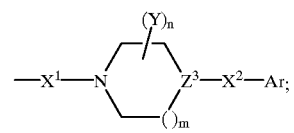

wherein
$X^1$ is CO or an isostere thereof;
m is 0 or 1;
Y is optionally substituted alkyl, optionally substituted aryl, or optionally substituted arylalkyl or two Y taken together may form an alkylene (2–3C) bridge;
n is 0, 1 or 2;
$Z^3$ is CH or N;
$X^2$ is CH, $CH_2$ or an isostere thereof; and Ar consists of one or two phenyl moieties directly coupled to $X^2$ optionally substituted by halo, nitro, alkyl (1–6C), alkenyl (1–6C), CN or $CF_3$, or by RCO, COOR, $CONR_2$, $NR_2$, OR, SR, OOCR or NROCR wherein R is H or alkyl (1–6C) or by phenyl, itself optionally substituted by the foregoing substituents;

$R^2$ is H, or alkyl (1–6C) optionally including one or more heteroatoms which are O, S or N, and optionally substituted by one or more of halo, OR, SR, $NR_2$, RCO, COOR, $CONR_2$, OOCR, or NROCR where R is H or alkyl (1–6C), or by CN or =O, or by an aliphatic or aromatic 5 or 6 membered ring optionally containing 1–2 N heteroatoms;

$R^3$ is H, halo, $NO_2$, alkyl (1–6C), alkenyl (1–6C), CN, OR, SR, $NR_2$, RCO, COOR, $CONR_2$, OOCR, or NROCR where R is H or alkyl (1–6C).

Thus, in one aspect, the invention is directed to compounds of the formulas set forth above. In other aspects, the invention is directed to methods to produce these compounds, to pharmaceutical compositions containing them, and to methods of treating inflammation using these compounds. The invention is also directed to treating conditions associated with cardiac failure using the invention compounds and other compounds described herein.

MODES OF CARRYING OUT THE INVENTION

The compounds of formulas 1–4 are useful in a variety of physiological contexts, as further described below. Preferred embodiments are those wherein both $Z^1$ and $Z^2$ are CH; thus, among the preferred compounds of the invention are derivatives of indole. Also preferred are those of forumulas (1) and (2); in embodiments wherein the compounds of the invention are substituted indoles, the substituent $R^1$ is thus in the 5-position. These compounds—i.e., those of formulas (1) and (2) wherein both $Z^1$ and $Z^2$ are CH are especially preferred. However, substituents may be placed at carbons in the 2- or 3-position of the indole ring. Especially preferred are substituents at the 3-position, especially those coupled through carboxarnide linkages.

Thus, preferred embodiments of $R^4$ are of the formula RNHCO- wherein R is alkyl or substituted alkyl.

In other preferred embodiments, the substituents shown for the compounds of the invention are as set forth below.

In regard to $R^1$:

$X^1$ is CO or an isostere thereof. Thus, in addition to CO, $X^1$ may be $CH_2$, SO, $SO_2$, or CHOH. CO is preferred.

$Z^3$ is CH or N; $Z^3$=CH is preferred.

Typically m is 1; however, in some compounds of the invention, m can be 0; thus, this substituent is a five-membered ring.

$X^2$ is $CH_2$ if Ar consists of a single phenyl moiety or CH if Ar consists of two phenyl moieties or may be an isostere thereof. Thus, for appropriate embodiments of Ar, $X^2$ may be any of the alternatives set forth above for $X^1$.

The phenyl moieties represented by Ar may optionally be substituted by substituents including alkyl (1–6C), halo, RCO, COOR, $CONR_2$, OR, SR, $NR_2$, OOCR, NROCR, $NO_2$, CN, or $CF_3$, wherein R is H or alkyl (1–6C). The phenyl moieties may also be substituted with an additional phenyl residue, preferably at the 4-position. The additional phenyl residue may itself be substituted with the substituents set forth above. The additional phenyl may be substituted in all five positions, but preferably less, preferably in 1–2 positions or not at all. Preferred substituents include halo and $OCH_3$. The substituents may occupy all five positions of the phenyl substituent, preferably 1–2 positions or the phenyl may be unsubstituted.

n may be 0, 1 or 2, and is preferably 0. However, when n is 1, Y is present and may be alkyl, arylalkyl or aryl, all of which may optionally be substituted by the substituents set forth above with regard to Ar. When n is 2, both Y groups together may constitute an alkylene bridge. A preferred bridge is an ethylene bridge. Preferred embodiments of Y when n is 1 include unsubstituted alkyl and unsubstituted arylalkyl.

With regard to $R^2$:

$R^2$ is preferably H, but may also be a suitable substituent. Such substituents are typically and preferably alkyl or substituted alkyl. The alkyl or substituted alkyl may optionally include a heteroatom which is O, N or S, preferably N. Permitted substituents are set forth above; preferred substituents include OR, where R is H or alkyl (1–6C) and =O. Also included among the preferred substituents are cylic moieties, such as piperazine, pyridine, piperidine, phenyl, and the like. Preferably, the alkyl embodiments of $R^2$ contain 0, 1 or 2 substituents.

With respect to $R^3$:

Although $R^3$ may be H, other embodiments are included and may be preferred. These include halo, OR, $NR_2$, and alkyl (1–6C), as particularly desirable.

The compounds of formulas (1)–(4) may be supplied in the form of their pharmaceutically acceptable acid-addition salts including salts of inorganic acids such as hydrochloric, sulfuric, hydrobromic, or phosphoric acid or salts of organic acids such as acetic, tartaric, succinic, benzoic, salicylic, and the like. If a carboxyl moiety is present, these compounds may also be supplied as a salt with a pharmaceutically acceptable base, including inorganic bases such as sodium hydroxide, potassium hydroxide, calcium hydroxide, ammonium hydroxide and the like or a salt with a organic base such as caffeine.

SYNTHESIS OF THE INVENTION COMPOUNDS

The compounds of the invention can be synthesized by a variety of methods most of them known in the art per se. The indole, benzimidazole, or benotriazole moiety may be supplied per se and the substituent $R^1$ coupled thereto. $R^1$ may be supplied as such, or its synthesis may be completed when the piperazyl or piperidyl residue is already coupled to the indole, benzimidazole or benotriazole moiety. Alternatively, especially in embodiments wherein $R^3$ represents a non-hydrogen substituent, the appropriately substituted p-aminobenzoic acid derivative may be cyclized and then substituted with piperazine or piperidine.

Thus, for example, as shown in Reaction Scheme 1, a piperazine protected with tert-butyloxycarbonyl (BOC) is coupled to 5-carboxybenzimidazole (or 5-carboxy-indole, or 5-carboxy-benzotrazole) in a reaction mixture containing a coupling agent such as EDAC in an inert, aprotic solvent to obtain the coupled carboxamide which is then deprotected and treated with substituted or unsubstituted benzyl halides or benzoyl halides.

substituted by $X^2$-Ar. In this reaction, the piperazyl or piperidyl derivative is directly reacted with the carboxylated bicycloheteroatom-containing nucleus in the presence of a coupling agent such as EDAC in the presence of an inert solvent as set forth above.

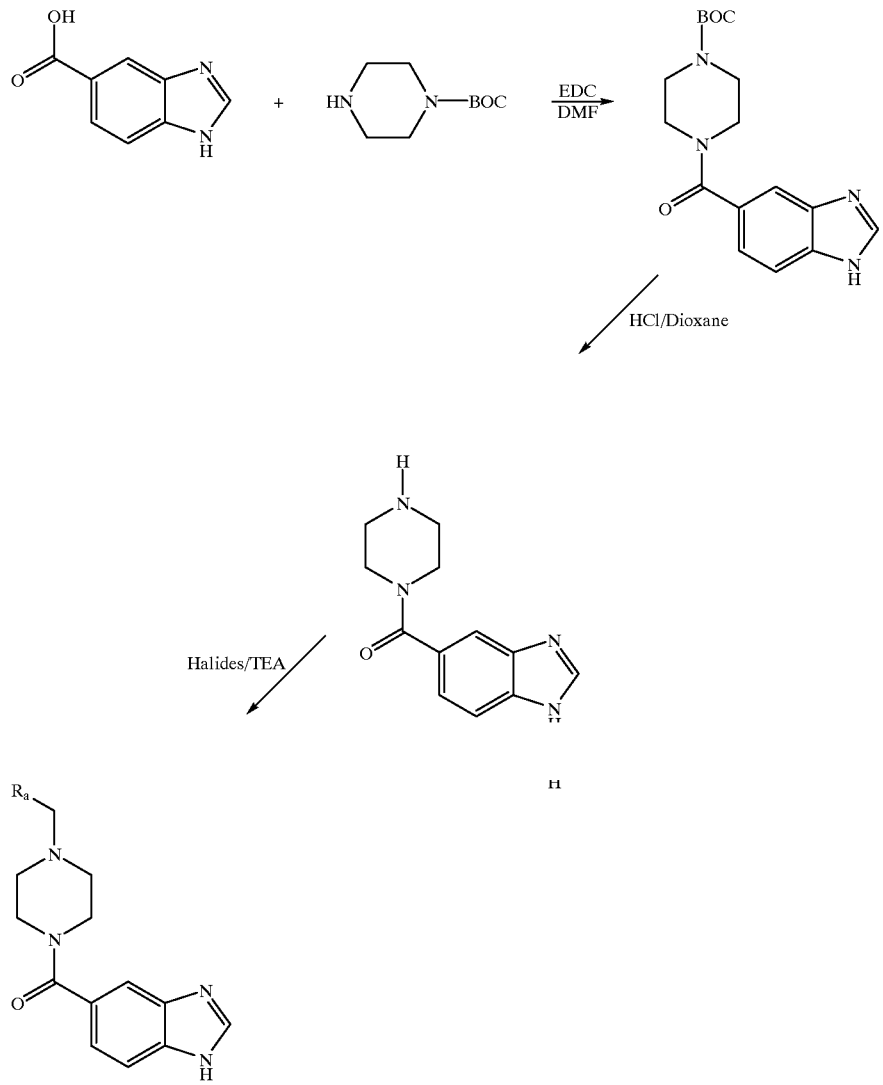

$R^a$=for example, 2,6-difluorophenyl; 3,4-difluorophenyl; 2,3-difluorophenyl; 3,5-difluorophenyl, 3-chiorophenyl; 4-chlorophenyl; 4-carboxymethylphenyl; 4-methoxyphenyl; 4-trifluoromethyloxyphenyl; 4methylphenyl; 6-chloropiperonyl; t-butylcarboxyphenyl; 3-trifluorophenyl; 2,4-dichilorophenyl; 3,4-dichlorophenyl; phenyl; methoxyphenyl; or p-toluyl.

Alternatively, as shown in Reaction Scheme 2, 5-carboxylated benzimidazole (or indole or benzotriazole) is reacted with a piperazine or piperidine moiety already

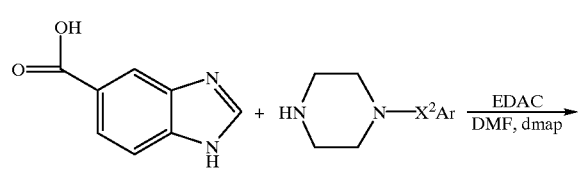

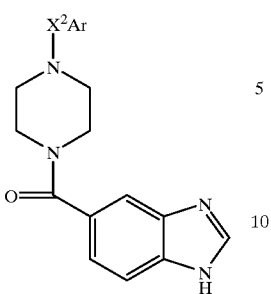

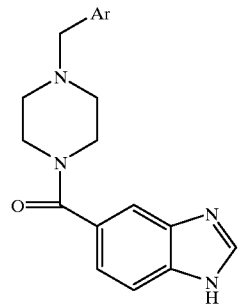

$X^2Ar$ = for example, 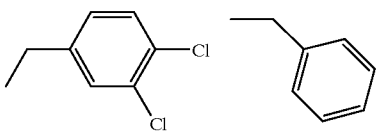

Ar = for example, 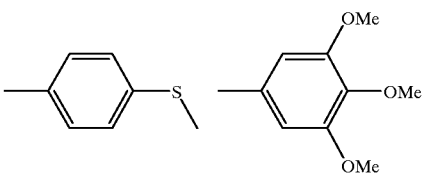

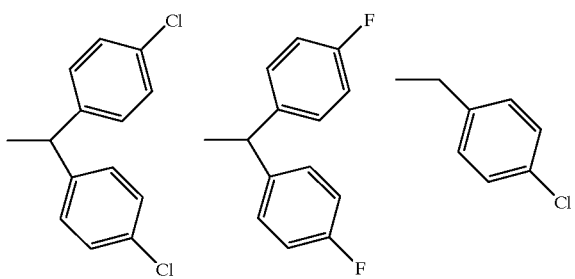

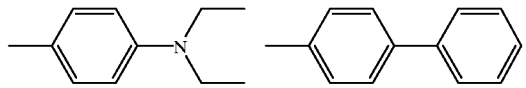

An alternative for coupling derivatized piperazine or piperidine to indole, benzimidazole or benzotriazole is shown in Reaction Scheme 4. In this reaction, the piperazine or piperidine ring is derivatized to a suitable leaving group as shown and then treated with a reducing agent such as NaH in an inert solvent to obtain the desired conjugate Scheme 4

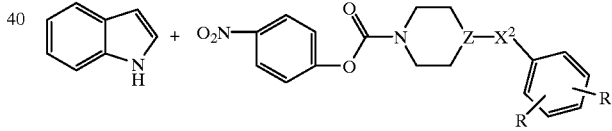

In order to form the substituted piperazine required for Scheme 2, piperazine is first converted to the BOC derivative and then reacted with ArCHO in the presence of a borohydride under acidic conditions to give the substituted piperazine as shown in Reaction Scheme 3.

Scheme 3

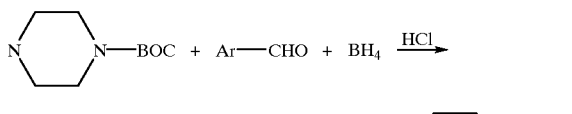

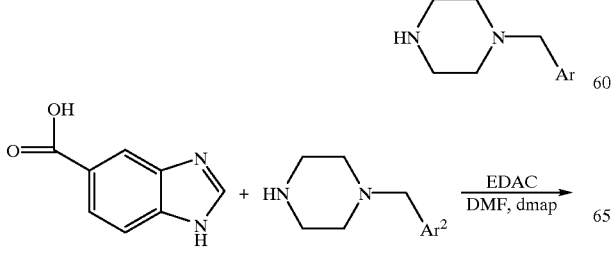

Another alternative is shown in Reaction Scheme 5. In this approach, a protected piperidone is reacted under reducing conditions with the appropriate phosphonate ester to obtain a protected benzylene piperidine. The product is then deprotected and reacted with the carboxylate of indole, benzimidazole or benzotriazole using an appropriate dehydrating agent. The product is then reduced to the desired arylalkylated piperidine derivative.

Scheme 5

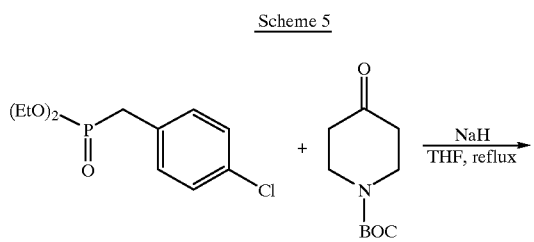

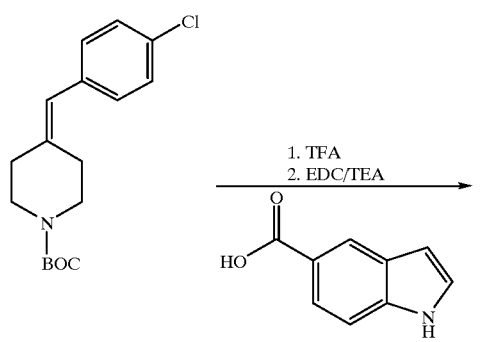

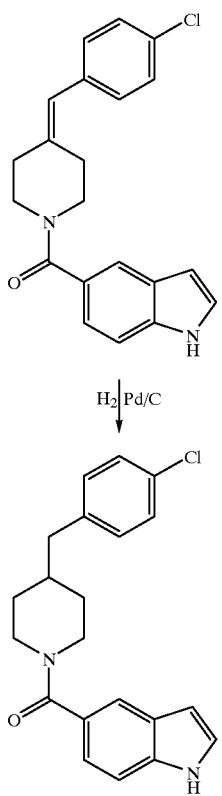

5-membered ring is reduced with Raney nickel and a mandatory methyl group included on the original aniline moiety is oxidized to the corresponding carboxylic acid. The resulting acid is then reacted with the desired piperidine or piperazine derivative in the presence of a coupling agent such as EDC.

Scheme 6

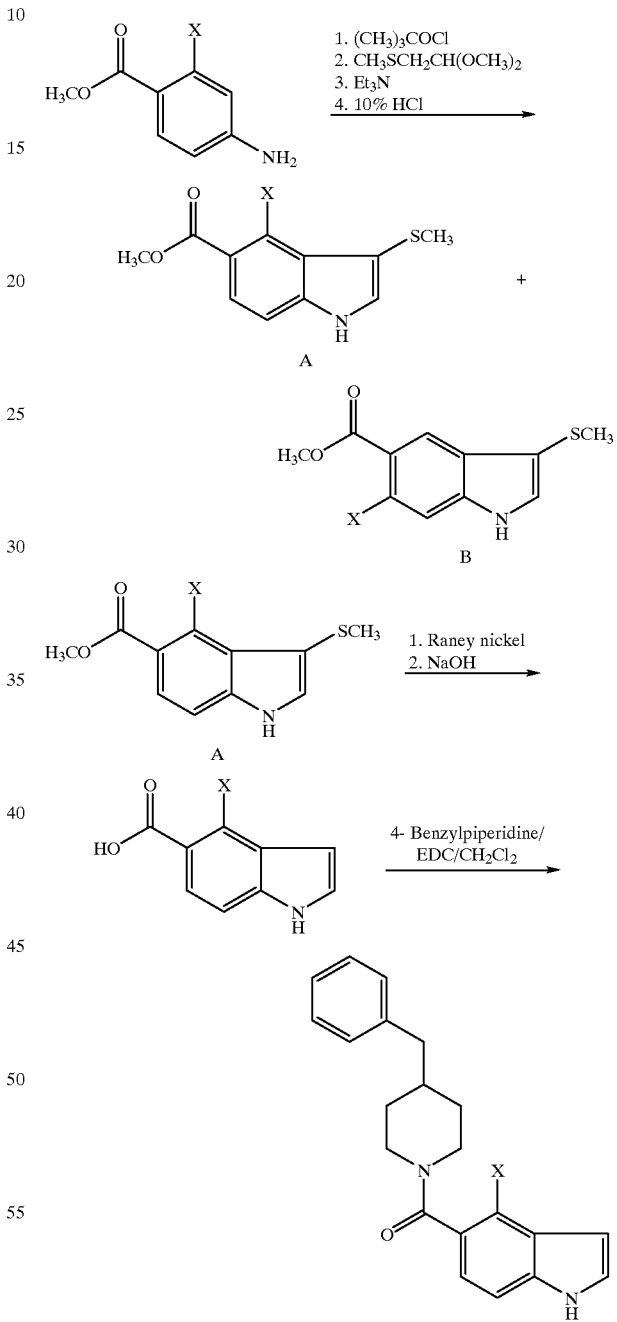

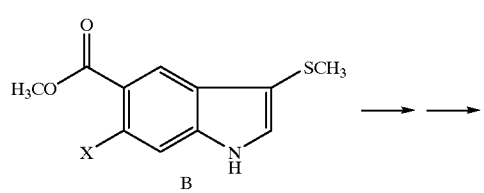

Reaction Scheme 6 illustrates a method for preparing compounds of the invention in which the indole is substituted in the 6-membered ring thereof. In Reaction Scheme 6, the appropriately substituted aniline is reacted with 1-methylmercaptyl-2,2-dialkoxyethane in the presence of tertiary butyryl chloride and base to provide the desired indole. Depending on the nature of the substitution of the aniline starting material, more than one isomer may result as shown. The methylmercaptyl group remaining on the

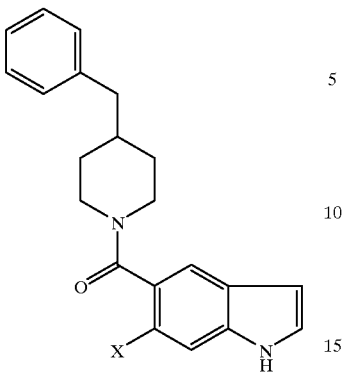

X = Cl, OCH₃, CH₃

Alkylation of the nitrogens on the indole, benzimidazole or benzotriazole nucleus in the compounds per se is canned out by conventional means using the halide of the substituent to be added in the presence of base and acetone.

Scheme 7

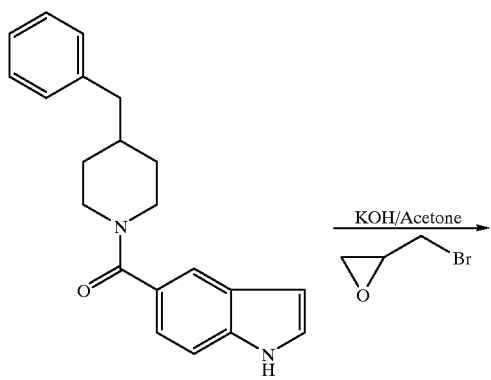

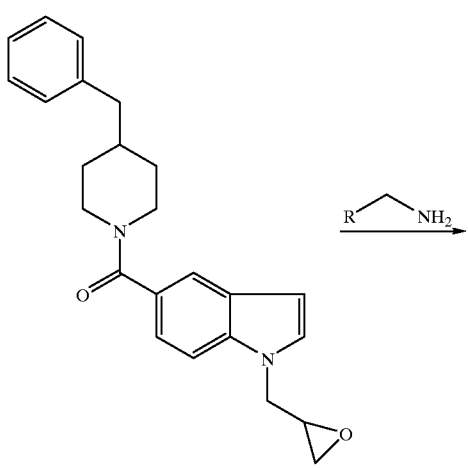

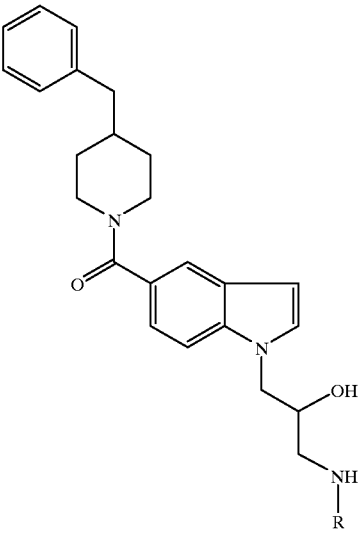

For synthesis of compounds wherein n is 1—i.e., wherein the piperidine ring contains one additional substituent other than those mandated in the compounds of the invention, the 4-substituted piperidine is first protected using BOC₂O in THF or other aprotic solvent and then reacted with, for example, an alkyl iodide in the presence of S-butyl lithium/TMEDA using, for example, ether as a solvent to produce the alkylated piperidine. The alkylated piperidine is then converted to the invention compound by deprotection followed by formation of the carboxamido linkage to the indoyl residue. This is exemplified below.

For compounds of the invention that are indoles substituted at the 3-position, the Reaction Scheme shown at the beginning of Example 23 may conveniently be used. Typically, the carboxamide starting material is treated with trifluoroacetic anhydride to obtain the trifluoroacetyl intermediate, which is also a compound of the invention. Upon treatment with base, the 3-carboxylic acid is formed which can then be reacted with a suitable amine to obtain additional compounds of the invention.

ADMINISTRATION AND USE

The compounds of the invention are useful in treating conditions associated with inflammation. Thus, the compounds of formulas (1)–(4) or their pharmaceutically acceptable salts are used in the manufacture of a medicament for prophylactic or therapeutic treatment of mammals, including humans, in respect of conditions characterized by excessive production of cytokines and/or inappropriate or unregulated cytokine activity on such cells as cardiomyocytes, cardiofibroblasts and macrophages.

The compounds of the invention inhibit the production of cytokines such as TNF, IL-1, IL-6 and IL-8, cytokines that are important proinflammatory constituents in many different disease states and syndromes. Thus, inhibition of these cytokines has benefit in controlling and mitigating many diseases. The compounds of the invention are shown herein to inhibit a member of the MAP kinase family variously called p38 MAPK (or p38), CSBP, or SAPK-2. The activation of this protein has been shown to accompany exacerbation of the diseases in response to stress caused, for example, by treatment with lipopolysaccharides or cytokines such as TNF and IL-1. Inhibition of p38 activity, therefore, is predictive of the ability of a medicament to provide a beneficial effect in treating diseases such as coronary artery disease, congestive heart failure, cardiomyopathy, myocarditis, vasculitis, restenosis, such as occurs following coronary angioplasty, atherosclerosis, rheumatoid arthritis, rheumatoid spondylitis, osteoarthritis, gouty arthritis and other arthritic conditions, multiple sclerosis, acute respiratory distress syndrome (ARDS), asthma, chronic obstructive pulmonary disease (COPD), silicosis, pulmonary sarcosis, sepsis, septic shock, endotoxic shock, toxic shock syndrome, heart and brain failure (stroke) that are characterized by ischemia and reperfusion injury, surgical procedures, such as transplantation procedures and graft rejections, cardiopulmonary bypass, coronary artery bypass graft, CNS injuries, including open and closed head trauma, inflammatory eye conditions such as conjunctivitis and uveitis, acute renal failure, glomerulonephritis, inflammatory bowel diseases, such as Crohn's disease or ulcerative colitis, graft vs. host disease, bone resorption diseases like osteoporosis, type II diabetes, pyresis, psoriasis, cachexia, viral diseases such as those caused by HIV, CMV, and Herpes, and cerebral malaria.

Within the last several years, p38 has been shown to comprise a group of MAP kinases designated p38α, p38β, p38γ and p38δ. Jiang, Y. et al. *J Biol Chem* (1996) 271:17920–17926 first reported characterization of p38β as a 372-amino acid protein closely related to p38α. Kumar, S. et al. *Biochem Biophys Res Comm* (1997) 235:533–538 and Stein, B. et al. *J Biol Chem* (1997) 272:19509–19517 reported a second isoform of p38β, p38β2, containing 364 amino acids with 73% identity to p38α. All of these reports show evidence that p38β is activated by proinflammatory cytokines and environmental stress, although the second reported p38β isoform, p38β2, appears to be preferentially expressed in the CNS, heart and skeletal muscle compared to the more ubiquitous tissue expression of p38α. Furthermore, activated transcription factor-2 (ATF-2) was observed to be a better substrate for p38β2 than for p38α, thus suggesting that separate mechanisms of action may be associated with these forms. The physiological role of p38β1 has been called into question by the latter two reports since it cannot be found in human tissue and does not exhibit appreciable kinase activity with the substrates of p38α.

The identification of p38γ was reported by Li, Z. et al. *Biochem Biophys Res Comm* (1996) 228:334–340 and of p38δ by Wang, X., et al., *J Biol Chem* (1997) 272:23668–23674 and by Kumar, S., et al., *Biochem Biophys Res Comm* (1997) 235:533–538. The data suggest that these two p38 isoforms (γ and δ) represent a unique subset of the MAPK family based on their tissue expression patterns, substrate utilization, response to direct and indirect stimuli, and susceptibility to kinase inhibitors.

Various results with regard to response to drugs targeting the p38 family as between p38α and either the putative p38β1 or p38β2 or both were reported by Jiang, Kumar, and Stein cited above as well as by Eyers, P. A. et al. *Chem and Biol* (1995) 5:321–328. An additional paper by Wang, Y. et al. *J Biol Chem* (1998) 273:2161–2168 suggests the significance of such differential effects. As pointed out by Wang, a number of stimuli, such as myocardial infarction, hypertension, valvular diseases, viral myocarditis, and dilated cardiomyopathy lead to an increase in cardiac workload and elevated mechanical stress on cardiomyocytes. These are said to lead to an adaptive hypertrophic response which, if not controlled, has decidedly negative consequences. Wang cites previous studies which have shown that in ischemia reperftision treated hearts, p38 MAPK activities are elevated in association with hypertrophy and programmed cell death. Wang shows in the cited paper that activation of p38β activity results in hypertrophy, whereas activation of p38α activity leads to myocyte apoptosis. Thus, selective inhibition of p38α activity as compared to p38β activity will be of benefit in treating conditions associated with cardiac failure. These conditions include congestive heart failure, cardiomyopathy, myocarditis, vasculitis, vascular restenosis, valvular disease, conditions associated with cardiopulmonary bypass, coronary artery bypass, grafts and vascular grafts. Further, to the extent that the α-isoform is toxic in other muscle cell types, α-selective inhibitors would be useful for conditions associated with cachexia attributed to TNF or other conditions such as cancer, infection, or autoimmune disease.

The compounds of the invention which selectively inhibit the activity of the p38α isoform are useful for treating conditions associated with activation of p38α, in particular those associated with cardiac hypertrophy, ischemia or other environmental stress such as oxidation injury, hyperosmolarity or other agents or factors that activate p38α kinase, or cardiac failure, for example, congestive heart failure, cardiomyopathy and myocarditis.

The manner of administration and formulation of the compounds of the invention will depend on the nature of the condition, the severity of the condition, the particular subject to be treated, and the judgement of the practitioner; formulation will depend on mode of administration. As the compounds of the invention are small molecules, they are conveniently administered by oral administration by compounding them with suitable pharmaceutical excipients so as to provide tablets, capsules, syrups, and the like. Suitable formulations for oral administration may also include minor components such as buffers, flavoring agents and the like. Typically, the amount of active ingredient in the formulations will be in the range of 5%–95% of the total formulation, but wide variation is permitted depending on the carrier. Suitable carriers include sucrose, pectin, magnesium stearate, lactose, peanut oil, olive oil, water, and the like.

The compounds useful in the invention may also be administered through suppositories or other transmucosal vehicles. Typically, such formulations will include excipients that facilitate the passage of the compound through the mucosa such as pharmaceutically acceptable detergents.

The compounds may also be administered topically, for topical conditions such as psoriasis, or in formulation intended to penetrate the skin. These include lotions, creams, ointments and the like which can be formulated by known methods.

The compounds may also be administered by injection, including intravenous, intramuscular, subcutaneous or intraperitoneal injection. Typical formulations for such use are liquid formulations in isotonic vehicles such as Hank's solution or Ringer's solution.

Alternative formulations include nasal sprays, liposomal formulations, slow- release formulations, and the like, as are known in the art.

Any suitable fonnulation may be used. A compendium of art-known formulations is found in *Remington's Pharma-* ceutical Sciences, latest edition, Mack Publishing Company, Easton, Pa. Reference to this manual is routine in the art.

The dosages of the compounds of the invention will depend on a number of factors which will vary from patient to patient. However, it is believed that generally, the daily oral dosage will utilize 0.001–100 mg/kg total body weight, preferably from 0.01–50 mg/kg and more preferably about 0.01 mg/kg–10 mg/kg. The dose regimen will vary, however, depending on the conditions being treated and the judgment of the practitioner.

As implicated above, although the compounds of the invention may be used in humans, they are also available for veterinary use in treating animal subjects.

The following examples are intended to illustrate but not to limit the invention.

EXAMPLES 1–3 ILLUSTRATE REACTION SCHEME 1

EXAMPLE 1

Preparation of 4-BOC piperazinyl-benzimidazole-5-carboxamide

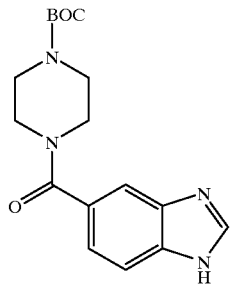

Benzimidazole-5-carboxylic acid (3.25 g, 20 mMol) was reacted with 2.52 g (20 mMol) diisopropylcarbodiimide in dry DMF at room temperature for 15 minutes. To this reaction mixture was added 3.75 g (20 mMol) t-butyl-1-piperazine carboxylate, and the mixture was stirred for 18 h. The mixture was poured into water and extracted with methylene chloride (3×100 mL). The combined extracts were washed again with water, brine and dried over MgSO$_4$. After removal of the solvent in vacuo, the residue was chromatographed on a column of silica gel eluting with CHCl$_3$-Methanol (gradient, methanol 0 to 5%) to yield 5.69 g (86 %) of the product. $^1$H-NMR (DMSO d$_6$): s 8.3 (1H); m 7.7–7.6 (2H), m 7.2–7.3 (1H), m 3.6–3.3 (8H) s 1.4 (9H); MS (ESI) m/e 330 (m$^+$).

EXAMPLE 2

Preparation of piperazinyl-benzimidazole-5-carboxamide

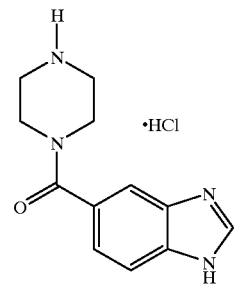

The N-BOC piperazinyl-benzimidazole-5-carboxamide (5.6 g) was stirred in 20 mL 4 Molar HCl-dioxane for 1 h. The dioxane was removed under reduced pressure to yield the hydrochloride salt in quantitative yield. This was used for alkylations without any further purifications.

EXAMPLE 3

Preparation of 4-(2,6-difluorobenzyl)-piperazinyl-benzymidazole-5-carboxamide

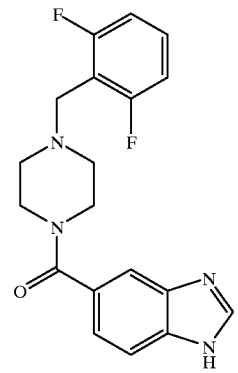

A. Piperazinyl-benzimidazole-5-carboxamide (0.186 g, 0.5 mMol) was taken in 5 mL DMF and 0.101 g (1 mMol) triethylamine was added and stirred for 15 minutes at room temperature. To this reaction mixture was added 0.104 g 2,6-difluorobenzyl bromide and the mixture was stirred for 20 h. This was poured into water and extracted with methylene chloride (3×50 mL). The combined extract was further washed with brine, water and dried over MgSO$_4$. The solvent was removed in vacuo and the residue chromatographed on silica gel eluting with chloroforn-methanol (0 to 5% methanol, gradient). Evaporation of the desired fraction gave 48.9 mg of the desired product; MS(ESI) m/e 356 (M$^+$).

B. Using the procedure set forth in paragraph A, the following compounds were prepared:

| Preparation of | By substituting for 2,6-difluorobenzyl bromide: |
|---|---|
| 4-(2,3-difluorobenzyl)-piperazinyl-benzimidazole-5-carboxamide MS (ESI) m/e 356 (M$^+$) | 2,3-difluorobenzyl bromide |
| 4-(3,5-difluorobenzyl)-piperazinyl-benzimidazole-5-carboxamide MS (ESI) m/e 356 (M$^+$) | 3,5-difluorobenzylbromide |
| 4-(3-chlorobenzyl)-piperazinyl-benzimidazole-5 carboxamide MS (ESI) m/e 354 (M$^+$) | 3-chlorobenzyl bromide |
| 4-(4-carboxymethyl benzyl)-piperazinyl-benzimidazole-5-carboxamide MS (ESI) m/e 378 (M$^+$) | methyl-4-(bromomethyl)-benzoate |
| 4-(4-methoxybenzyl)-piperazinyl-benzimidazole-5-carboxamide MS (ESI) m/e 350 (M$^+$) | 4-methoxybenzyl chloride |
| 4-(4-trifluoromethoxybenzyl)-piperazinyl-benzimidazole-5-carboxamide MS (ESI) m/e 404 (M$^+$) | 4-(4-trifluoromethoxy)-benzyl bromide |
| 4-(4-methylbenzyl)-piperazinyl-benzimidazole-5-carboxamide MS (ESI) m/e 334 (M$^+$) | 4-methylbenzyl bromide |
| 4-(6-chloropiperonyl)-piperazinyl-benzimidazole-5-carboxamide MS (ESI) m/e 399 (M$^+$) | 6-chloropiperonyl chloride |
| 4-(4-t-butylcarboxymethyl)-piperazinyl-benzimidazole-5-carboxamide MS (ESI) m/e 344 (M$^+$) | t-butyl bromoacetate |
| 4-(2,4-dichlorobenzoyl)-piperazinyl-benzimidazole-5-carboxamide MS (ESI) m/e 403 (M$^+$) | 2,4-dichlorobenzoyl chloride |
| 4-(3,4-dichlorobenzoyl)-piperazinyl-benzimidazole-5-carboxamide MS (ESI) m/e 403 (M$^+$) | 3,4-dichlorobenzoyl chloride |
| 4-(3-cyclopentylpropionyl)-piperazinyl-benzimidazole-5-carboxamide MS (ESI) m/e 354 (M$^+$) | 3-cyclopentylpropionyl chloride |
| 4-(cyclohexylcarbonyl)-piperazinyl-benzimidazole-5-carboxamide MS (ESI) m/e 340 (M$^+$) | 3-cyclohexanecarbonyl chloride |
| 4-[trans-3-(trifluoromethyl)-cinnamoyl]-piperazinyl-benzimidazole-5-carboxamide MS (ESI) m/e 428 (M$^+$) | trans-3-(trifluoromethyl)-cinnamoyl chloride |
| 4-(4-chlorobenzoyl)-piperazinyl-benzimidazole-5-carboxamide MS (ESI) m/e 369 (M$^+$) | 4-chlorobenzoyl chloride |
| 4-benzoylpiperazine-benzimidazole-5-carboxamide MS (ESI) m/e 334 (M$^+$) | benzoyl chloride |
| 4-(2-trifluoromethylbenzoyl)-piperazinyl-benzimidazole-5-carboxamide MS (ESI) m/e 402 (M$^+$) | 2-(trifluoromethyl)-benzoyl chloride |
| 4-(4-methxybenzoyl)-piperazinyl-benzimidazole-5-carboxamide MS (ESI) m/e 364 (M$^+$) | 4-methoxybenzoyl chloride |

EXAMPLE 4 ILLUSTRATES REACTION SCHEME 2

EXAMPLE 4

Preparation of 4-(3,4-dichlorophenyl)-piperazinyl-benzimidazole-5-carboxamide

A. Benzimidazole-5-carboxylic acid (1 mMol, 162 mg) was dissolved in 5 mL dry DMF and reacted with 1-ethyl-3-(3-dimethylaminopropyl)-carbodiimide hydrochloride for 15 minutes. 1-(3,4-dichlorophenyl)-piperazine, 1 mMol (231 mg) was added followed by 10 mg DMAP. The mixture was stirred for 20 h at room temperature. The reaction mixture was poured into water and extracted with methylene chloride (3×50 mL). The extracts were combined, washed with brine, water and dried over MgSO$_4$. After evaporation of the solvent, the residue was chromatographed on silica gel with chloroform-methanol (0–5% methanol, gradient). Evaporation of the desired fractions gave 150 mg (40%) of the title compound; MS (ESI) m/e 375 (M$^+$).

B. Using the procedure of paragraph A, the following were prepared:

| Preparation of | Substituting for 1-(3,4-dichlorophenyl) piperazine, |
|---|---|
| 4-(4-chlorobenzhydryl)-piperazinyl-benzimidazole-5-carboxamide MS (ESI) m/e 431 (M$^+$) | 1-(4-chlorobenzhydryl)-piperazine |
| 4-trans-1-cinnamyl piperazinyl-benzimidazole-5-carboxamide MS (ESI) m/e 346 (M$^+$) | trans-1-cinnamyl piperazine |
| 4-(4-chlorophenyl)-piperazinyl-benzimidazole-5-carboxamide MS (ESI) m/e 341 (M$^+$) | 1-(4-chlorophenyl)-piperazine |
| 4-[bis(4-fluorophenyl)-methyl]-piperazinyl-benzimidazole-5-carboxamide MS (ESI) m/e 432 (M$^+$) | 1-Bis (4-fluorophenyl)-methyl piperazine |
| 4-(4-chlorobenzyl)-piperazinyl-benzimidazole-5-carboxamide MS (ESI) m/e 354 (M$^+$) | 1-(4-chlorobenzyl)-piperazine |
| 4-(2-chlorobenzyl)-piperazinyl-benzimidazole-5-carboxamide MS (ESI) m/e 354 (M$^+$) | 1-(2-chlorobenzyl)-piperazine |
| 4-benzylpiperazinyl-benzimidazole-5-carboxamide MS (ESI) m/e 320 (M$^+$) | 1-benzyl piperazine |

EXAMPLE 5 ILLUSTRATES REACTION SCHEME 3

EXAMPLE 5

Preparation of 4-(4-methylthiobenzyl)-piperazinyl-benzimidazole-5-carboxamide

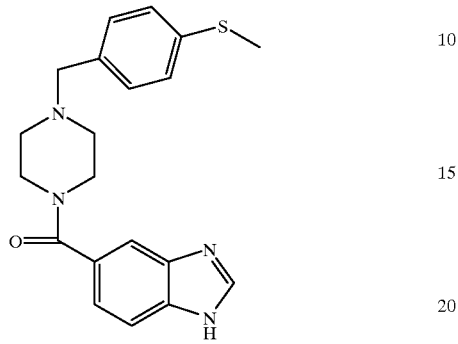

| Preparation of | Substituting for 4-(methylthio)-benzaldehyde |
|---|---|
| 4-(3,4,5-trimethoxybenzyl)-piperazynyl-benzimidazole-5-carboxamide MS (ESI) m/e 410 (M⁺) | 3,4,5-methoxybenzaldehyde |
| 4-(2-naphthylmethyl)-piperazynyl-benzimidazole-5-carboxamide MS (ESI) m/e 370 (M⁺) | 2-naphthaldehyde |
| 4-(4-diethylaminobenzyl)-piperazinyl-benzimidazole-5-carboxamide MS (ESI) m/e 391 (M⁺) | 4-diethylaminobenzaldehyde |
| 4-(biphenylmethyl)-piperazinyl-benzimidazole-5-carboxamide MS (ESI) m/e 396 (M⁺) | 4-biphenylcarboxaldehyde |
| 4-(4-Phenoxybenzyl)-piperazinyl-benzimidazole-5-carboxamide MS (ESI) m/e 412 (M⁺) | 4-phenoxybenzaldehyde |
| 4-(4-quinolinylmethyl)-piperazinyl-benzimidazole-5-carboxamide MS (ESI) m/e 371 (M⁺) | 4-quinolinecarboxaldehyde |

A. A mixture of 4-(methylthio)-benzaldehyde, 305 mg (2 mMol) and N-BOC piperazine, 372 mg (2 mMol) was stirred in dry methanol for 30 minutes. To this mixture was added 1.6 g of polymer-supported borohydride (2.5 mMol/g, on Amberlite, IRA-400, Aldrich) and the mixture was stirred for 24 h. The polymer was removed by filtration and evaporation of the solvent yielded the 4-BOC-1-(4-methylthio)-benzylpiperazine in quantitative yield. MS (ESI) m/e 322, (M⁺).

The 4-BOC-1-(4-methylthio)-benzylpiperazine was taken in 10 mL 1:1 TFA/methylene chloride and stirred for 1 h at room temperature. The solvents were removed in vacuo and the residue was used without purification for coupling with benzimidazole-5-carboxylic acid.

Benzimidazole-5-carboxylic acid (2 mMol, 324 mg) was taken in 15 mL dry DMF and reacted with 2 mMol (382 mg) EDAC at room temperature for 15 minutes. The above described 1-(4-methylthio)-benzylpiperazine was added as a DMF solution followed by 505 mg (5 mMol) TEA. The mixture was stirred for 20 h. The mixture was poured into water and extracted with methylene chloride (3×50 mL). The combined extracts were washed with brine, water and dried over MgSO₄. The solvent was removed in vacuo and the residue was chromatographed. Evaporation of the desired fractions gave the title compound; MS (ESI) m/e 366 (M⁺).

B. Using the procedure of paragraph A, the following were prepared:

EXAMPLE 6

Preparation of 4-benzyl-piperidinyl-benzimidazole-5-carboxamide

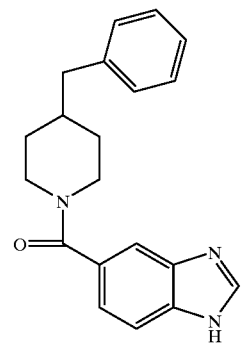

Benzimidazole-5-carboxylic acid (1.62 g, 10 mMol) was reacted with EDAC (1.92 g, 10 mMol) in 40 mL dry DMF at room temperature for 15 minutes. To the reaction mixture was added 4-benzylpiperidine (1.75 g, 10 mMol) and DMAP (~20mg, catalyst) and the mixture was stirred at room temperature for 20 h. It was poured into water and extracted with methylene chloride (3×100 mL). The combined extract was washed with water, brine and again with water. The extract was dried over MgSO$_4$ and evaporated. The residue was chromatographed on a column of silica gel with chloroform-methanol (0 to 5% methanol). Evaporation of the desired fractions gave 1.5 g (47%) of the product after recrystallization from ethyl acetate-hexane. $^1$HNMR (CDCl$_3$): δ=7.8 (s, 1H); 7.1–7.3 (m, 8H); 4.8–4.7 (broad m, 1H), 3.7–3.9 (broad m, 1H); 3.1–2.7 (broad m, 2H); 2.55 (d, 2H); 2.0–1.1 (m, 5H). MS (ESI) m/e 319 (M$^+$), 318 (M$^+$-H).

EXAMPLE 7

N-propylation of 4-benzyl-piperidinyl-benzimidazole-5-carboxamide

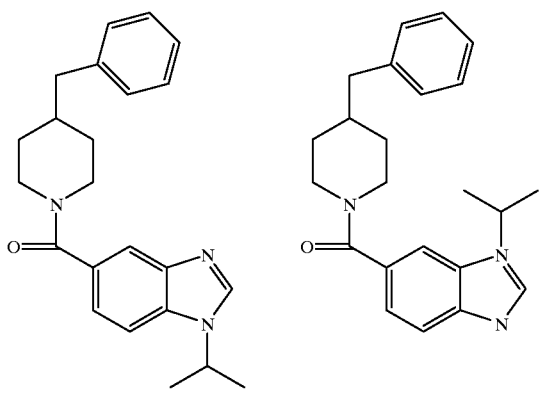

4-(4-Benzyl)-piperidinyl-benzimidazole-5-carboxamide (318 mg, 1 mMol) was taken in 20 mL acetone. KOH (solid, 280 mg, 5 mMol) was added followed by 2-iodopropane (1 g~6 mMol) and the mixture was refluxed for 20 h. The acetone was removed in vacuo and the residue extracted from water with methylene chloride (3×50 mL). The extract was dried, evaporated and the residue chromatographed on silica gel with CHCL$_3$-Methanol (0 to 3% methanol). MS (ESI) m/e 360 (M$^+$). HPLC: (Vydac C18 column, 5 to 40% acetonitrile/water containing 0.1% TFA) two peaks showing both isomers.

EXAMPLE 8

Preparation of 4-benzylpiperidinyl-indole-5-carboxamide

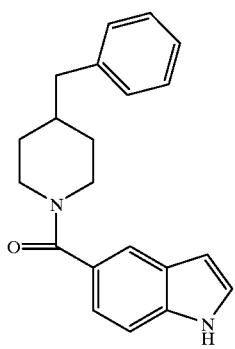

Indole-5-carboxylic acid (1.61 g,10 mMol) was reacted with EDAC (1.92 g, 10 mMol) in 40 mL dry DMF for 15 minutes. 4-Benzylpiperidine (1.75 g, 10 mMol) was added followed by DMAP (20 mg, catalyst ) and the reaction mixture was stirred for 20 h. The mixture was poured into water and extracted with methylene chloride (3×100 mL). The combined extract was washed with dilute hydrochloric acid, saturated sodium bicarbonate and water and dried over MgSO$_4$. After evaporation of the solvent, the residue was chromatographed with methylene chloride-methanol (0 to 2% methanol, gradient) to yield 1.60 g (50%) of the product after recrystallization from ether-Hexane. MS (ESI) m/e 318 (M$^+$), (317$^+$-H). $^1$HNMR (CDCl$_3$) δ=8.5 (s, 1H); 7.7 (s, 1H); 7.4–7.15 (m, 8H); 6.8 (s, 1H); 4.8–4.6 (br, m, 1H); 4.1–3.99br, m, 1H); 3.1–2.7 (br, m, 2H); 2.6 (d, 2H); 1.9–1.7 (br, m, 3H); 1.4–1,2 (br, m, 2H).

EXAMPLE 9

Preparation of 4-benzylpiperidinyl-1-(2-propyl)-indole-5-carboxamide

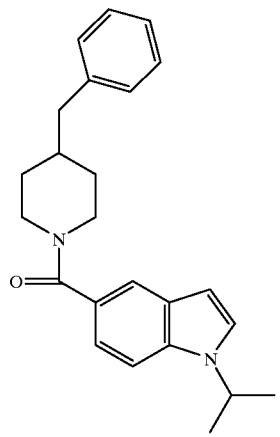

A mixture of 4-benzylpiperidinyl-benzimidazole-5-carboxamide (318 mg, 1 mMol), solid KOH (280 mg, 5 mMol) and 2-iodopropane (1 g, 6 mMol) was refluxed in 20 mL acetone for 20 h. After the removal of acetone in vacuo, the residue was extracted from water with methylene chloride (3×50 mL). The combined extract was dried, evaporated and chromatographed to yield 180 mg (50%) of the desired product. $^1$HNMR (CDCl$_3$): δ=7.7 (s, 1H); 7.4–7.1 (m, 7H); 4.8–4.6 (m, 1H); 3.0–2.7 (br, m, 4H); 2.6 (d, 2H); 1.8–1.45 (m, 3H); 1.5 (d, 6H); 1.3–1.1 (m, 2H). MS (ESI) m/e 360 (M).

EXAMPLE 10

Preparation of 4-(4-chlorobenzyl)-piperazinyl-1-(2-propyl)-indole-5-carboxamide

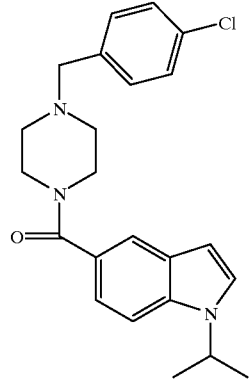

4-(4-Chlorobenzyl)piperazinyl-indole-5-carboxamide (420 mg, 1.32 mMol) was taken in acetone. Solid KOH (280 mg, 5 mMol) was added followed by the addition of 2-iodopropane (1 g, 6 nMol) and the mixture was refluxed with stirring for 20 h. Acetone was removed in vacuo and the residue was extracted from water using methylene chloride. The extract was dried and evaporated and the residue was chromatographed on a column of silica gel using ethylacetate-hexane (ethylacetate 0 to 25%, gradient) and recrystallized from ether-hexane to yield 300 mg of the product. $^1$HNMR (CDCl$_3$): δ=7.6 (s, 1H); 7.3–7.1 (m, 6H); 6.5 (s, 1H); 4.65–4.55 (m, 1H); 3.8–3.5 (m, 4H); 3.4 (s, 2H); 2.4–2.5 (s, 4H); 1.5 (d, 6H). MS (ESI) m/e 395 (M$^+$).

EXAMPLE 11

Preparation of Additional Analogs

Using the procedure of Example 8, following are prepared:

| Preparation of | Using the procedure set forth in Example 8, but substituting for indole-5-carboxylic acid |
|---|---|
| 4-benzylpiperidinyl-indole-6-carboxamide MS (ESI) m/e 318 (M$^+$), (317$^+$-H) | Indole-6-carboxylic acid |
| 4-benzylpiperidinyl-benzotriazole-5-carboxamide MS (ESI) m/e 320 (M$^+$), (319$^+$-H) | Benzotriazole-5-carboxylic acid |

Using the procedure of Example 10, these compounds were alkylated, e.g.,

| Preparation of | Using the procedure set forth in Example 11, but substituting for 4-chlorobenzyl piperidinyl indole-5-carboxamide |
|---|---|
| 4-benzylpiperidinyl-1-(2-propyl)-indole-6-carboxamide MS (ESI) m/e 360 (M$^+$) | 4-benzyl piperidinyl-indole-6-carboxamide |
| 4-benzylpiperidinyl-1- | 4-benzyl piperidinyl-benzotriazole-5- |
| (2-propyl)-benzotriazole-5-carboxamide | carboxamide |

EXAMPLE 12

Preparation of 3-Chlorobenzylpiperazinyl-N-benzyl-benzimidazole-5- and 6-carboxamides A. This paragraph describes the procedure for formation of the N-benzyl derivatives of the compounds of the invention; succeeding paragraphs describe alkylation with other moieties.

3-Chlorobenzylpiperazinyl-benzimidazole-5-carboxamide (0.12 g, 0.33 mMol) and the benzyl bromide (0.058 g, 0.33 mMol) in 15 mL DMF were combined with K$_2$CO$_3$ (0.09 g, 0.66 mMol). The mixture was stirred at RT overnight, then heated at 45° C. for 3 h. EtOAc was added and washed with water. The organic layer was evaporated and the isomers were separated by silica gel column chromatography using 5% MeOH in EtOAc. of isomer a (70 mg, 48%), MS (ESI) m/e 444 (M$^+$) and of isomer b (40 mg, 27%), MS (ESI) m/e 444 (M$^+$) were obtained.

B. 3-Chlorobenzylpiperazinyl-N-(2-propyl)-benzimidazole-5- and 6-carboxamides.

3-Chlorobenzylpiperazinyl-benzimidazole-5-carboxamide was alkylated substituting 2-iodopropane for benzyl bromide in paragraph A. The isomers were separated using the same chromatographic conditions. Isomer a, MS (ESI) m/e 396 (M$^+$).; isomer b, MS (ESI) m/e 396 (M$^+$).

C. 3-Chlorobenzylpiperazinyl-N-methyl-benzimidazole-5- and 6-carboxamide

3-Chlorobenzylpiperazinyl)-benzimidazole-5-carboxamide was alkylated substituting iodomethane for benzyl bromide in the procedure of paragraph A. The isomers were separated using silica gel column chromatography using 50% acetone in acetonitrile as the eluting solvent. Isomer a, MS (ESI) m/e 368 (M$^+$), isomer b, MS (ESI) m/e 368 (M$^+$).

Similarly, 4-benzylpiperidinyl-(1-methyl)-indole-5-carboxamide (MS (ESI) m/e 332 (M$^+$)) was prepared from 4-benzylpiperidinyl-indole-5-carboxamide.

D. 3-Chlorobenzylpiperazinyl-N-ethyl-benzimidazole-5- and 6-carboxamides

3-Chlorobenzylpiperazinyl-benzimidazole-5-carboxamide was alkylated substituting iodoethane for benzyl bromide in paragraph A. Isomer a, MS (ESI) m/e 382 (M$^+$); isomer b, MS (ESI) m/e 382 (M$^+$).

Similarly, 4-benzylpiperidinyl-(1-ethyl)-indole-5-carboxamide (MS (ESI) m/e 346 (M$^+$)) was prepared from 4-benzylpiperidinyl-indole-5-carboxamide.

EXAMPLE 13

Preparation of 4-(4-chlorobenzyl)-piperidinyl-indole-5-carboxamide

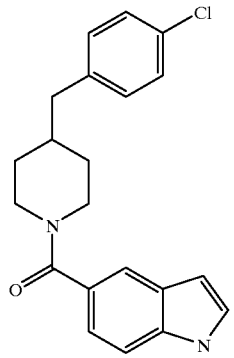

This example illustrates Reaction Scheme 5.

A. Preparation of N-BOC-4-(4-chlorobenzylene)-piperidine

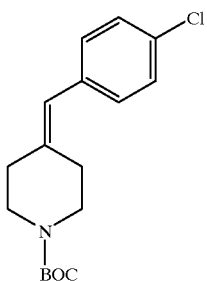

N-BOC-4-piperidone (2.0 g; 10 mmol) was taken with diethyl-4-chlorobenzylphosphonate (2.6 g; 10 mmol) in dry THF. Sodium hydride (400 mg, 60% dispersion in mineral oil; 10 mmol) was added and the mixture was refluxed for three hr. The THF was removed in vacuo and the residue extracted from water with methylene chloride. The extract was dried over $MgSO_4$, evaporated and the residue was chromatographed on silica gel to yield 0.615 g of the desired product. $^1$HNMR (CDCl$_3$): δ=7.3 (d, 2H); 7.1 (d, 2H); 6.3 (s, 1H); 3.55–3.50 (m, 2H); 3.45–3.35 (m, 2H); 2.45–2.35 (m, 2H); 2.30–2.25 (m, 2H); 1.25 (s, 9H). EIMS: 307 (M$^+$), 251 (M$^+$-C3H8).

B. Coupling of 4-Chlorobenzylene piperidine with indole-5-carboxylic acid

The N-BOC-4- (4-chlorobenzylene-piperidine, described above, was deprotected by stirring in 20 mL 1:1 dichloromethane-trifluoroacetic acid for 1 h. It was evaporated and dried in vacuo for 1 h to remove all traces of trifluoroacetic acid. It was redissolved in 15 mL dichloromethane and the TFA salt was neutralized by the addition of a slight excess of triethylamine. Solution A.

Indole-5-carboxylic acid 0.32 g (2 mmol) was reacted with 0.383 g EDAC in 30 mL dry dichloromethane for 15 minutes. To this solution was added the methylene chloride solution of 4-chlorobenzylene-piperidine (solution A) followed by the addition of 10 mg of DMAP. The mixture was stirred for 20 h. The mixture was washed with water, 2N HCl, 5% sodium carbonate and then water. The organic solution was dried, evaporated and the residue was chromatographed on silica gel eluting with ethylacetate-hexane (1:4). Yield: 260 mg (37%). EIMS: 350 (M$^+$), 315 (M$^+$-Cl)

$^1$HNMR (CDCl$_3$): δ=8.4 (s, 1H); 7.7 (s, 1H); 7.3–7.0 (m, 7H); 6.5 (s, 1H); 6.25 (s, 1H); 3.8–3.0 (m, br, 4H); 2.6–2.20 (m, br, 4H).

C. Hydrogenation of 4-(4-chlorobenzylene)-piperidine-indole-5-carboxamide 4-(4-Chlorobenzylene)-piperidine-indole-5-carboxamide (240 mg, 0.68 mmol) was dissolved in 40 mL THF. Pd/C (25 mg) was added and the mixture was hydrogenated (1 atm) for 20 h with rapid stirring. The catalyst was removed by filtration through celite and the organic solution was evaporated and the residue was recrystallized from methylene chloride/hexane. Quantitative yield. EIMS: 352 (M$^+$), 351 (M$^+$-H).

EXAMPLE 14

Using the general procedure set forth in Example 13, the following are prepared:

| Preparation of | Substituting for 4-chlorobenzyl piperidine |
|---|---|
| 4-(3-chlorobenzyl)-piperidinyl-indole-5-carboxamide MS (ESI) m/e 353 (M$^+$) | 3-chlorobenzyl piperidine |
| 4-(2-chlorobenzyl)-piperidinyl-indole-5-carboxamide MS (ESI) m/e 353 (M$^+$) | 2-chlorobenzyl piperidine |

EXAMPLE 15

Synthesis of cis-2-Methyl-4-phenylpiperidine-1-yl-indole-5-carboxamide

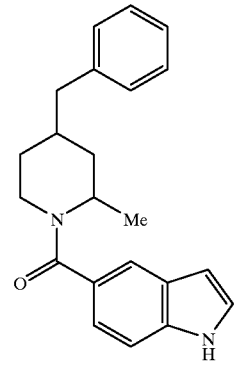

A. A mixture of 4-benzylpiperidine (3.52 mL, 20.0 mMol) and di-tert-butyl-dicarbonate (5.45 g, 25.0 mMol) in 100 mL of THF was refluxed for 20 h. After cooling to rt the reaction mixture was poured into water and extracted with ethyl acetate (2×100 mL). the combined organic extract was washed with water and brine. The extract was dried over $Na_2SO_4$ and evaporated. The residue was chromatographed on a column of silica gel with 10% ethyl acetate-hexane. Evaporation of the desired fractions gave 5.02 g (91%) of the product as an oil. MS (ESI) m/e 275 (M$^+$).

B. A mixture of 1-BOC4-benzylpiperidine (0.825 g, 3.0 mMol) and N,N,N',N',-tetramethylethylenediamine (TMEDA) (0.59 mL, 3.9 mMol) in 6 mL of Et$_2$O was cooled to −78° C. under argon. A 1.3M solution of s-BuLi in cyclohexane (3.0 mL, 3.9 mMol) was added dropwise. After the addition was complete, the reaction mixture was stirred at −20° C. for 30 min and cooled back to −78° C. Methyl iodide (0.28 mL, 4.5 mMol) was added and the reaction mixture was stirred at −78° C. for 5 min, the cooling bath removed and stirring was continued an additional 3 min. The reaction mixture was poured into water and extracted with ethyl acetate (2×25 mL). The combined organic extract was washed with water and brine. The extract was dried over $Na_2SO_4$ and evaporated to give 0.58 g (67%) of an oil that was one spot by TLC (silica gel, 10% ethyl acetate-hexane). This material was used directly in the next step. MS (ESI) m/e 289 (M+).

C. To a solution of 1-BOC-2-methyl-4-benzylpiperidine (0.29 g, 1.0 mMol) in 5 mL of dichloromethane was added trifluoroacetic acid (TFA) (0.5 mL). After stirring at rt for 10 h the reaction mixture was evaporated in vacuo and azeotroped twice with dichloromethane and twice with hexane. The residue was dissolved in 5 mL of dichloromethane and diisopropylethylamine (1.6 mL, 10 mMol) was added. In a separate flask a mixture of 5-indolecarboxylic acid (0.19 g, 1.2 mMol) and EDAC (0.23 g, 1.2 mMol) was dissolved in 15 mL of dichloromethane and stirred at rt for 5 min. To this reaction mixture was added the first solution, and the resulting mixture stirred at rt for 20 h. The reaction mixture was poured into water and extracted with ethyl acetate (2×50 mL). The combined organic extract was washed with water and brine. The extract was dried over $NASO_4$ and evaporated. The residue was chromatographed on a column of silica gel with 1% MeOH-dichloromethane. Evaporation of the desired fractions gave 0.18 g (54%) of the product as an oil.

When tested as described below, the title compound has an $IC_{50}$=280 nM.

EXAMPLE 16

Preparation of 4-Chloro-(4-benzylpiperidinyl)indole-5-carboxamide and 6-Chloro-(4-benzylpiperidinyl)indole-5-carboxamide

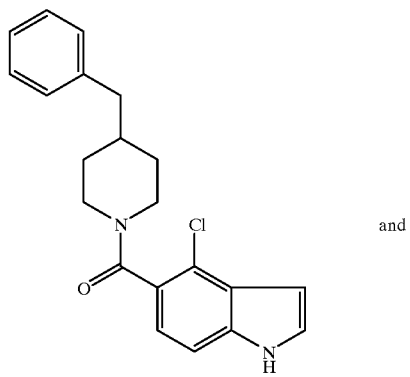

and

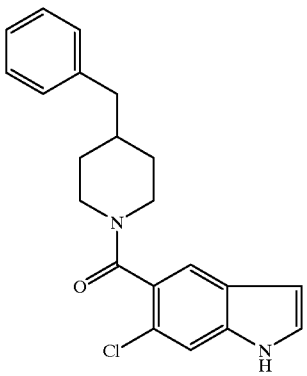

A. The indole synthesis was accomplished by the method of Gassman, P. G. *J Am Chem Soc* (1974) 96: 5495–5507. To a solution of 2.0 g (10.8 mmol) of 4-amino-2-chloro methylbenzoate in 30 mL $CH_2Cl_2$ at −60° C. was added 1.2 g (10.8 mmol) of t-butyl hypochlorite in 20 mL of $CH_2Cl_2$. After 10 min. 10.8 mmol of methylthioacetaldehyde dimethyl acetal in 10 ml of $CH_2Cl_2$ was added, stirring at −60° C. continued for 1 h. Subsequently, 10.8 mmol of $Et_3N$ in 10 ml $CH_2Cl_2$ was added and the solution was allowed to warm to room temperature. The solvent was evaporated and the residue was dissolved in 30 mL $CCl_4$, 5 mL of $Et_3N$ was added and the mixture was refluxed for 4 h. The solvent was removed and the residue was dissolved in 50 mL of ether. Cyclization of the acetal to indole was effected by stirring this solution for 3 h with 20 mL of 2 N HCl. The ethereal layer was washed with saturated $NaHCO_3$, dried, filtered and evaporated. The isomeric indoles were separated by column chromatography on silica gel. The structure of the isomers was identified by NMR spectroscopy. Isomer a: 5-carboxymethyl-4-chloro-3-thiomethylindole, $^1H$ NMR ($CDCl_3$) δ2.35 (s, 3H), 3.95 (s, 3H), 7.32 (s, 1H), 7.42 (s, 1H), 8.33 (s, 1H), 8.61 (s, 1H). Isomer b: 5-carboxymethyl-6-chloro-3-thiomethylindole, $^1H$ NMR ($CDCl_3$) δ2.42 (s, 3H), 3.97 (s, 3H), 7.20 (s, 1H), 7.25 (d, 1H), 7.71 (d, 1 H), 8.58 (s, 1H).

A solution of 100 mg of 5-carboxymethyl-4-chloro-3-thiomethylindole (isomer a) in 10 mL of ethanol was treated with W-2 Raney nickel until dethiomethylation was completed. The indole ester isolated was treated with NaOH in methanol:water (1:1) and thereby 60 mg of 4-chloro-indole-5-carboxylic acid was isolated as a white solid, $^1H$ NMR (DMSO-$d_6$) δd 6.61 (s, 1H), 7.41 (d, 1H), 7.52 (s, 1H), 7.62 (d, 1H), 11.62 (s, 1H).

To a solution of 50 mg (0.25 mmol) of above indole acid in 10 mL of DMF was added 50 mg (0.28 mmol) of 4-benzylpiperidine and 60 mg (0.28 mmol) of EDAC. The reaction mixture was stirred overnight, diluted with ethyl acetate and washed with water. the organic layer was dried, filtered and evaporated to get a white solid. This was purified by silica gel chromatography followed by crystallization to obtain 50 mg of 4-chloro-5-(4-benzylpiperidinyl)-indole carboxamide as a white solid, MS (M+352).

Isomer b was converted to 6-chloroindole-5-carboxylic acid using the same reaction sequence as described above and was coupled to 4-benzylpiperidine to obtain 6-chloro- 5-(4-benzylpiperidinyl)-indole carboxamide as a white solid, MS (M+352).

B. Using the method of paragraph A, 4-Chloro-(4-(4-fluorobenzyl)piperidinyl)indole-5-carboxamide and 6-Chloro-(4-(4-fluorobenzyl) piperidinyl)indole-5-carboxamide were prepared.

EXAMPLE 17

Preparation of 4-Methoxyindole and 6-methoxyindole-5-carboxylic acids.

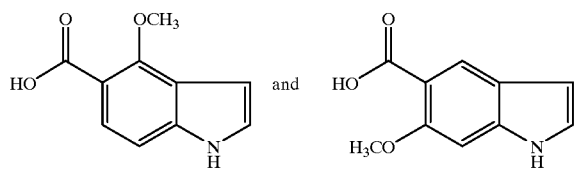

The corresponding methyl esters of these indole acids were prepared by a modified method of Scheme 6 according to Inoue, S. *Heterocycles*, (1992) 34: 1017–1029, wherein the two isomeric indole acids were obtained in a 3:2 ratio. 5-carboxymethyl-4-methoxyindole. $^1$H NMR (CDCl$_3$) δ2.42 (s, 3H), 3.92 (s, 3H), 4.13 (s, 3H), 7.14 (d, 1H), 7.18 (d, 1H), 7.55 (d, 1H), 9.41 (s, 1H). 5-Carboxymethyl 6-methoxyindole. $^1$H NMR (CDCl$_3$) δ2.38 (s, 3H), 3.81 (s, 3H), 3.95 (s, 3H), 6.83 (s, 1H), 7.21 (s, 1H), 8.22 (s, 1H), 8.50 (s, 1H).

EXAMPLE 18

Preparation of 4-Methoxy-(4-benzylpiperidinyl) indole-5-carboxamide and 6-Methoxy-(4-benzylpiperidinyl)indole-5-carboxamide

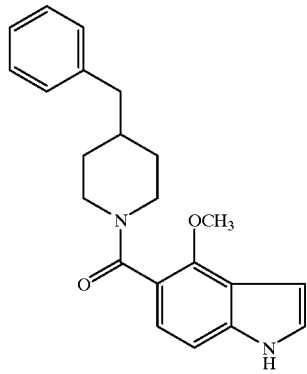

and

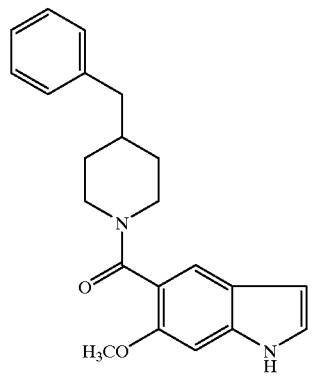

4-Methoxy or 6-methoxy-indole-5-carboxylic acid was coupled with 4-benzylpiperidine to obtain the title compounds, MS (M+349).

In addition, 4-methoxy-indole-5-carboxylic acid was coupled with 4-(4-fluorobenzyl)piperidine to obtain 4-methoxy-(4-(4-fluorobenzyl)piperidinyl)indole-5-carboxamide, MS (M+367) and 6-methoxy-indole-5-carboxylic acid was coupled with 4-(4-fluorobenzyl) piperidine to obtain 6-methoxy-(4-(4fluorobenzyl) piperidinyl)indole-5-carboxamide. MS (M+367).

EXAMPLE 19

Preparation of N-(3-cyclohexylmethylamino-2-hydroxypropyl)-4-benzylpiperidinyl-indole-5-carboxamide

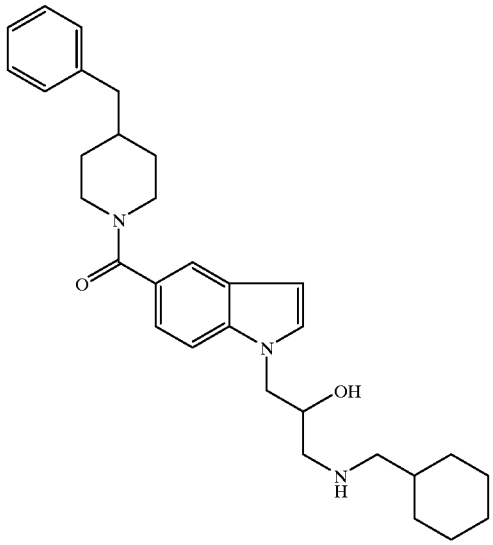

A. The title compound was prepared according to scheme 7. To an ice-cold solution of 1.0 g (3.0 mmol) of 4-benzylpiperidinyl indole-5-carboxamide in acetone was added 15 mmol of powdered KOH followed by 3.0 mmol of epibromohydrin and the mixture was stirred for 30 min. The mixture was filtered and the solution was evaporated. The residue was dissolved in ethyl acetate, washed with water, dried and evaporated. After purification by silica gel column chromatography 435 mg of epoxide was obtained. MS ($M^+$373).

To a solution of 200 mg (0.54 mmol) of the above indole epoxide in 5 mL of MeOH was added 121 mg (1.1 mmol) of cyclohexylmethylamine and the mixture was refluxed for 1 hr. The crude product was purified on silica gel column . The amino compound was then converted into its HCl salt by treating with ethanolic HCl. MS ($M^+$487).

B. Following the procedure of paragraph A, but substituting piperazine for cyclohexylmethylamine, N-(3-N-methylpiperazinyl-2-hydroxypropyl)-4-benzylpiperidinyl indole-5-carboxamide:

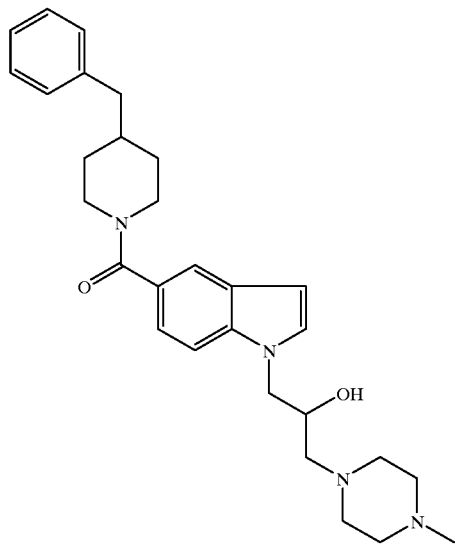

was prepared. MS ($M^+$473);

substituting benzylamine for cyclohexylmethylamine N-(3-benzylamino-2-hydroxypropyl)-4-benzylpiperidinyl indole-5-carboxamide:

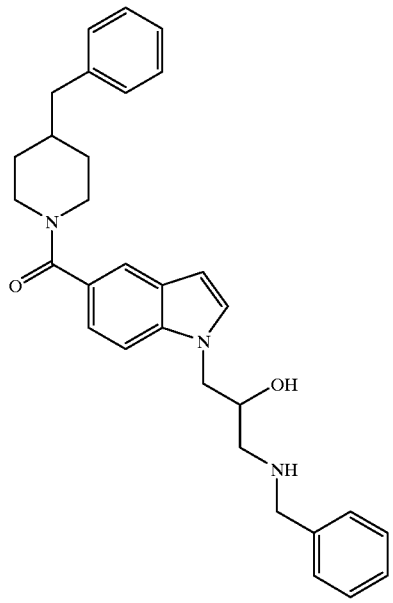

MS ($M^+$481) was prepared;
   substituting p-methoxybenzylamine for cyclohexylmethylamine, N-[3-{(4-methoxybenzyl)-amino}-2-hydroxypropyl-]5-(4-benzylpiperidinyl indole-5-carboxamide:

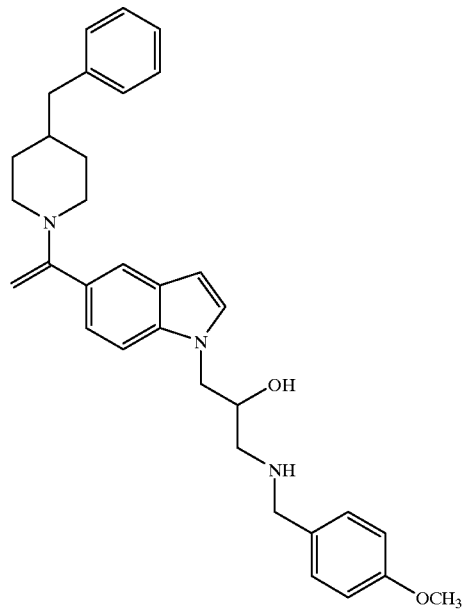

MS (M+511) was prepared; and
   substituting propylamine for cyclohexylmethylamine, N-{3-n-propylamino-2-hydroxypropyl}-4-benzylpiperidinyl indole-5-carboxamide:

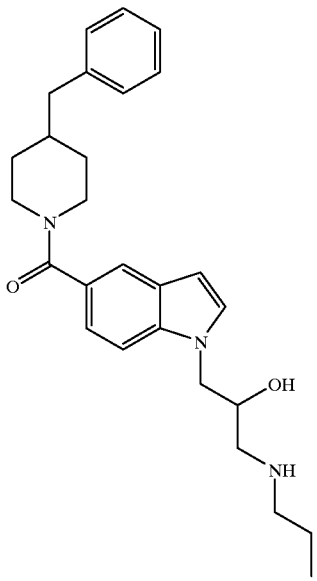

MS (M$^+$) 433 was prepared.

EXAMPLE 20

Preparation of N-(4-pyridoyl)4-benzylpiperidinyl indole-5-carboxamide

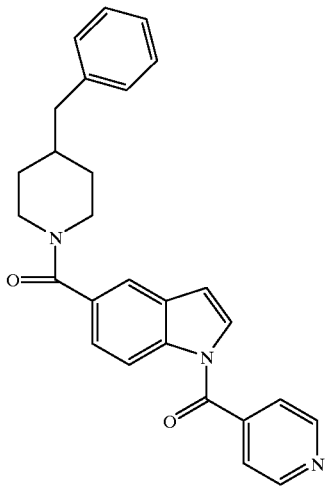

A. 0.318 mg (1 mmol) of 4-benzylpiperidinyl indole-5-carboxamide was dissolved in 15 mL dry DMF. 80 mg (60% suspension in oil) of sodium hydride was added and the mixture was stirred for 30 minutes under nitrogen. The mixture was cooled to 0° C. and 200 mg (1.1 mmol) isonicotinyl chloride hydrochloride was added and the mixture was stirred for 20 hr at room temperature. The reaction was quenched by the addition of sat. ammonium chloride solution, diluted with water and the product was extracted with dichloromethane. The extract was dried, evaporated and the residue was chromatographed on silica gel (ethyl acetate-hexane, gradient, 50–75% ethyl acetate) to yield 150 mg of the pure product. ESI MS (M$^+$423, M$^+$-H, 422).

B. Using the procedure of paragraph A, but substituting 4-picolyl chloride hydrochloride for isonicotinyl chloride hydrochloride, N-(4-pyridylmethyl)-4-benzylpiperidinyl indole-5-carboxamide:

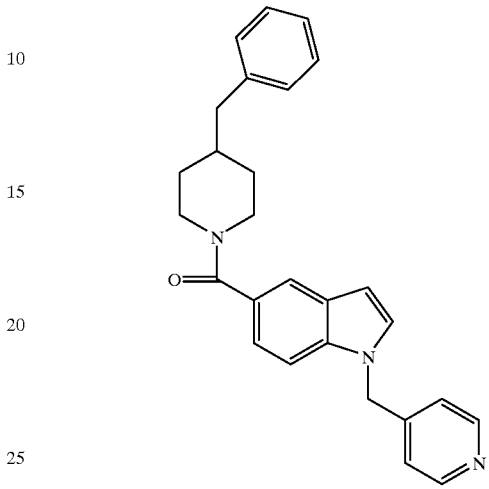

MS (M+409) was prepared.

EXAMPLE 21

Preparation of N-methylacetyl-4-Benzylpiperidinyl indole-5-carboxamide and its free acid

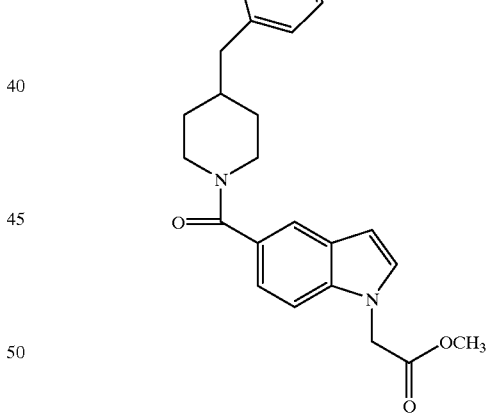

A. 1.95 g (6.13 mmol) of 4-benzylpiperidinyl indole-5-carboxamide was dissolved in 30 mL dry DMF and was treated with 320 mg (8 mmol, 60% suspension in oil) sodium hydride for 30 minutes. The reaction mixture was cooled to 0° C. and 1.225 g (8 mmol) bromomethylacetate was added and stirring continued for 1 h at 0° C. The ice-bath was removed and stirring continued for another 6 h at room temperature. The reaction was quenched by the addition of sat. ammonium chloride solution, diluted with water and extracted with dichloromethane. The extract was dried, evaporated and the residue purified by column chromatography on silica gel eluting with ethylacetate-hexane (25 –35% ethylacetate) to yield 2.2 g ( 92%) of the desired product. MS: M+, 390; M+-1, 389. $^1$HNMR (CDCl$_3$): ☐ 7.7 (s, 1H); 7.35–7.1 (m, 8H); 6.6 (s, 1H); 5.1 (s, 2H); 3.75 (s, 3H); 3.0–2.7 (br, m, 4H); 2.6 ( d, 2H); 1.9–1.2 9m, 5H).

B. 2.15 g, (5.5 mmol) of 4-Benzylpiperidinyl indole-5-carboxamide-1-methylacetate from paragraph A was taken in 20 mL ethanol . A solution of 2.0 g K$_2$CO$_3$ in 20 mL water was added and the mixture was refluxed for 2 h. The ethanol was removed under reduced pressure, the remaining solution diluted with water and acidified with conc. HCl. The precipitated product was collected by filtration, washed with water and dried to yield 1.9 g of the product. MS: M+, 376; M+-H, 375.

EXAMPLE 22

Preparation of 4-Benzylpiperidinyl indole-5-carboxamide-1-acetic acid-n-propylamide

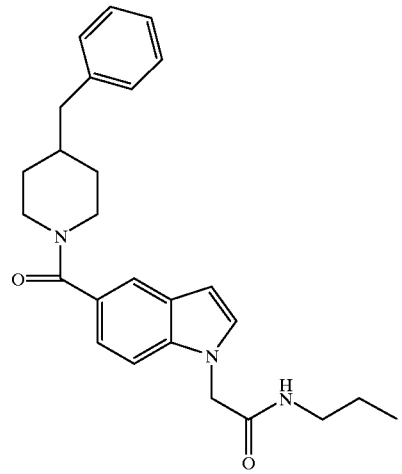

A. 4-Benzylpiperidinyl-indole-5-carboxamide-1-acetic acid (200 mg, 0.53 mmol) from Example 21 was reacted with 120 mg (0.61 mmol) EDC in 10 mL dry dichloromethane for 30 minutes. n-propylamine (100 μL, excess) was added and the mixture stirred for 20 h. The solution was diluted with dichloromethane, washed with water and 5% sodium carbonate solution. The organic solution was dried and evaporated and the residue purified by silica gel chromatography with ethyl acetate-hexane (3:2) to yield 100 mg of the product. MS (M+417).

B. Following the procedure of paragraph A, but substituting p-methoxybenzylamine for n-propylamine, 4-benzylpiperidinyl -indole-5-carboxamide-1-acetic acid, (4-methoxybenzyl) amide:

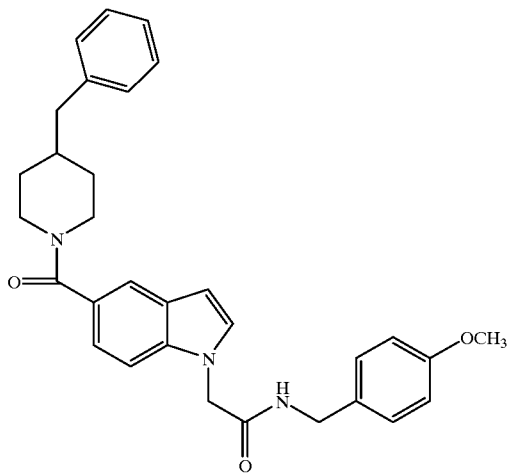

MS, ESI: M+H, 496 was prepared.

EXAMPLE 23

Preparation of 3-Substituted Indoles

The general procedure for synthesis of the 3-substituted indoles is outlined as follows:

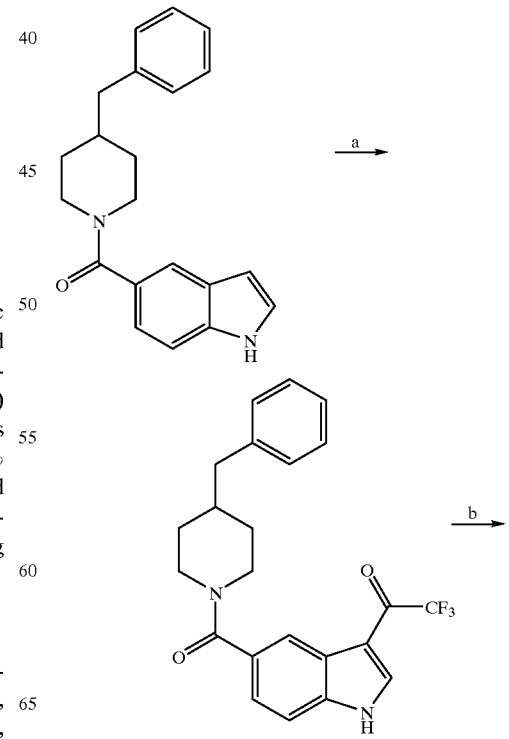

-continued

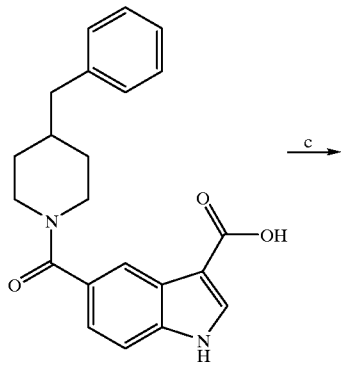

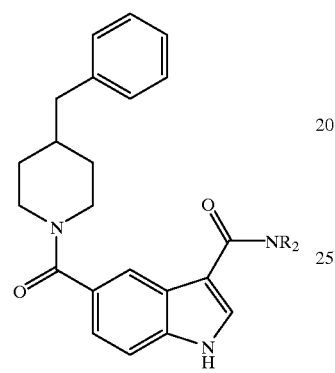

a) Trifluoroacetic anhydride, THF, 0° C., 3 hr.
b) aq. NaOH, reflux, 3-6 hrs.
c) R₂NH, EDAC./HCl, DMAP, DCM/DMF, 3-6 hrs.

A. 3-trifluoroacetyl-4-benzylpiperidinyl-indole-5-carboxamide: 4-benzyl piperidinyl-indole-5-carboxamide (1 eq.) was dissolved in anhydrous THF. The reaction vessel was purged with nitrogen and placed in an ice bath. Trifluoroacetic anhydride (1.2–1.3 eq.) was added via syringe. The reaction was allowed to continue at 0° C., until no more starting material was discovered by thin layer chromatography. In some cases the addition of additional trifluoroacetic anhydride was required to facilitate the completion of the reaction. After completion of the reaction, the reaction mixture was concentrated and redissolved in the minimal amount of ethyl acetate for chromatography using silica. The crude material was chromatographed using ethyl acetate and hexanes (1:1). The identity of the product 3-trifluoroacetyl-4-benzyl piperidinyl indole-5-carboxamide was determined by electron impact mass spectroscopy. (MH⁺413 (exp. 414, base peak 240.)

Similarly, using, as the starting material, 4-benzyl piperidinyl indole-6-carboxamide or 6-methoxy-(4-benzyl piperidinyl)indole-5-carboxamide, the corresponding 3-trifluoroacetyl derivatives were prepared.

B. 4-benzylpiperidinyl indole-5-carboxamide-3-carboxylic acid: The trifluoroacetyl indole derivative from paragraph A was suspended in aqueous sodium hydroxide (10 N, 5–6 eq.) And brought to reflux. Upon commencement of reflux a minimal amount of methanol was added to facilitate solubility. The reaction mixture was maintained at reflux for 3–6 hrs. Upon completion the reaction mixture was cooled to room temperature and diluted with water, and washed with ether. The aqueous layer was then acidified to pH4 with conc. HCl while placed in an ice bath. The acid was then extracted into ethyl acetate and washed with said. Sodium chloride solution, dried over anhydrous sodium sulfate and concentrated to give a solid. This solid was purified by chromatography on silica using ethyl acetate-:hexanes:methanol:acetic acid, 5:5:1:0.1. The identity of the product was determined by electron impact mass spectroscopy. (MH⁺361 (exp. 361), 317, base peak 144.)

Similarly, the additional 3-fluoroacetyl derivatives prepared in paragraph A were converted to the corresponding 3-carboxylic acids C. 3-(2-dimethylamino)ethylaminocarboxamidyl-(4-benzylpiperidinyl)indole-5-carboxarnide: The carboxylic acid of paragraph B (1 eq.) was treated with 1.1 equivalent of EDAC.HCl and 1 eq. Of dimethylaminoethylenediamine in the presence of a catalytic amount of DMAP in DMF/DCM 1:1 for 3–6 hrs. The reaction mixture was then concentrated and taken up in ethyl acetate. After washing with 5% aq. Sodium carbonate and a solution of saturated sodium chloride, the organic layer was dried over anhydrous sodium sulfate and concentrated to give crude material. This crude material was purified by chromatography on silica. The identity of the product, shown below, was determined by electron impact mass spectroscopy. (MH⁺432 (exp. 432).)

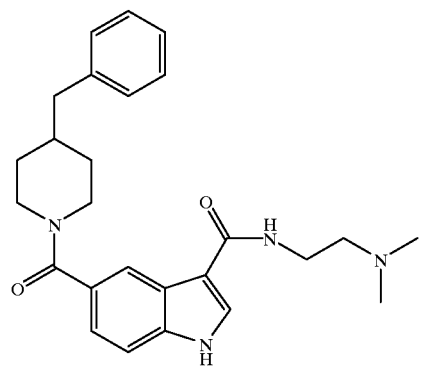

Similarly, making the appropriate substitutions for the carboxamnide and for the reactive amnine, the following compounds of the invention were prepared according to the reaction scheme set forth at the beginning of this example.

3-(2 metlioxyethylamnocarboxaniidyl)-(4-benzylpiperidinyl)indole-5-carboxamide;

3-(2-methylamninoethylaminocarboxamidyl)-(4-benzylpiperidinyl)indole-5-carboxamide;

3-(2-aminoethylaminocarboxamidyl)-(4-benzylpiperidinyl)indole-5-carboxamide;

3-(4-benzylpiperidinylcarboxamidyl)-(4-benzylpiperidinyl)indole-5-carboxamide 3-(4-benzylpiperidinylcarboxamidyl)-(4-benzylpiperidinyl)indole-6carboxamide 3-(4-fluorobenzylaminocarboxamidyl)-(4-benzylpiperidinyl)indole-5-carboxamide 3-2-(3,5-dimethoxyphenyl)ethylaminocarboxamidyl-(4-benzylpiperidinyl)indole-5-carboxamide;

3-trifluoroacetyl-(4-benzylpiperidinyl)indole-5-carboxamide;

6-methoxy-3-(2-dimethylaminoethylamino)carboxamidyl-(4-benzylpiperidinyl)indole-5-carboxamide;

EXAMPLE 24

Assay for p38 Kinase Inhibition

The compounds to be tested were solubilized in DMSO and diluted into water to the desired concentrations. The p38 kinase was diluted to 10 μg/ml into a buffer containing 20 mM MOPS, pH 7.0, 25 mM beta-glycerol phosphate, 2 mg/ml gelatin, 0.5 mM EGTA, and 4 mM DTT.

The reaction was carried out by mixing 20 μl test compound with 10 μl of a substrate cocktail containing 500 μg/ml peptide substrate and 0.2 mM ATP (+200 μCi/ml gamnma-32P-ATP) in a 4× assay buffer. The reaction was initiated by the addition of 10 μl of p38 kinase. Final assay conditions were 25 mM MOPS, pH 7.0, 26.25 mM beta-glycerol phosphate, 80 mM KCl, 22 mM $MgCl_2$, 3 mM $MgSO_4$, 1 mg/ml gelatin, 0.625 mM EGTA, 1 mM DTT, 125 μg/ml peptide substrate, 50 μM ATP, and 2.5 μg/ml enzyme. After a 40 minute incubation at room temperature, the reaction was stopped by the addition of 10 μl per reaction of 0.25 M phosphoric acid.

A portion of the reaction was spotted onto a disk of P81 phosphocellulose paper, the filters were dried for 2 minutes and then washed 4× in 75 mM $H_3PO_4$. The filters were rinsed briefly in 95% ethanol, dried, then placed in scintillation vials with liquid scintillation cocktail.

Alternatively, the substrate is previously biotinylated and the resulting reactions are spotted on SAM²™ streptavidin filter squares (Promega). The filters are washed 4× in 2M NaCl, 4× in 2M NaCl with 1% phosphoric acid, 2× in water, and briefly in 95% ethanol. The filter squares are dried and placed in scintillation vials with liquid scintillation cocktail.

Counts incorporated are determined on a scintillation counter. Relative enzyme activity is calculated by subtracting background counts (counts measured in the absence of enzyme) from each result, and comparing the resulting counts to those obtained in the absence of inhibitor. $IC_{50}$ values were determined with curve-fitting plots available with common software packages. Approximate $IC_{50}$ values were calculated using formula $$IC_{50}(app) = A \times i/(1-A)$$

where A=fractional activity and I=total inhibitor concentration.

EXAMPLE 25

Activity of the Invention Compounds

The activity of the invention compounds was tested as described above. The compounds tested were 4-benzylpiperidinyl or 4benzylpiperazinyl indole-5- or 6-carboxarnides. In general, the piperidinyl derivative was superior to the corresponding piperazinyl. The $IC_{50}$ for inhibition of p38 alpha is shown in Table 1.

TABLE 1

| Ring position | Piperidinyl $IC_{50}$ μM | Piperazinyl $IC_{50}$ μM |
|---|---|---|
| 5 | 0.150 | 1.71 |
| 6 | 0.462 | 5.52 |

The same compounds were tested for their specificity for p38α as compared to p38β. The results are shown in Table 2.

TABLE 2

| | Piperidinyl | | | Piperazinyl | | |
| Ring position | P38-β $IC_{50}$ μM | p38α $IC_{50}$ μM | $IC_{50}$ ratio β/α | P38-β $IC_{50}$ μM | p38-α $IC_{50}$ μM | $IC_{50}$ ratio β/α |
|---|---|---|---|---|---|---|
| 5 | 3.02 | 0.150 | 20.1 | 25.8 | 1.71 | 15.1 |
| 6 | 3.83 | 0.462 | 8.27 | 39.1 | 5.52 | 7.08 |

The compounds of the invention, generally, are specific for p38α as compared to p38-β: It is seen that the specificity for α as opposed to β is generally of the order of ten-fold.

The specificity of the compounds of the invention was also tested with respect to other kinases, including p38-γ, ERK-2, PKA, PKC, cdc-2, EGF-R, and DNA-PK as shown in Table 3. The compounds tested are the 4-benzylpiperidinyl indole-5- and 6-carboxamides with the number indicating the ring position of the carboxamide.

TABLE 3

| KINASE | $IC_{50}$ μM 5 | $IC_{50}$ μM 6 |
|---|---|---|
| p38-α | 0.150 | 0.462 |
| p38-γ | 228 | >300 |
| ERK-2 | >300 | >300 |
| PKA | 430 | >500 |
| PKC | >500 | >500 |
| cdc2 | >500 | >500 |
| EGF-R | >500 | >500 |
| DNA-PK | >500 | 450 |

The results are given in terms of approximate $IC_{50}$ (μM) values when the compounds were tested at 50 μM except for p38α which is based on $IC_{50}$ curves.

As shown, all of the compounds tested are highly specific for p38α as compared to these additional kinases.

Table 4 shows the inhibition of p38α by invention compounds that are 4-(benzylpiperidinyl)indole-5-carboxymides or 4-[(4-fluorobenzyl)piperidinyl]indole-5-carboximides, i.e., compounds of formulas (1) or (2):

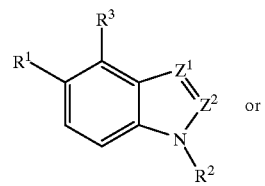

(1)

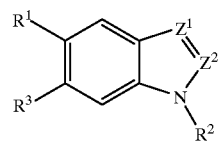

(2)

wherein $R^1$ is of formula (5) or (6):

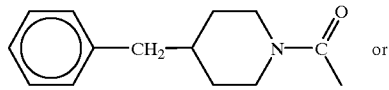

(5)

-continued

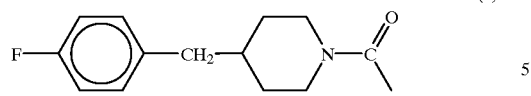

(6)

5

The values given are IC$_{50}$ in $\mu$M.

TABLE 4

| Formula | R$^3$ | R$^1$ | R$^2$ | Z$^1$ | Z$^2$ | IC$_{50}$ |
|---|---|---|---|---|---|---|
| 1 | H | (5) | H | N | CH | 0.635 |
| 1 | H | (5) | H | CH | CH | 0.523, 0.577 |
| 2 | CH$_3$O | (6) | H | CH | CH | 0.159 |
| 2 | Cl | (5) | Et$_2$N(CH$_2$)$_3$ | CH | CH | 0.199 |
| 1 | H | (6) | Et$_2$N(CH$_2$)$_2$ | CH | CH | 0.354 |
| 2 | CH$_3$O | (5) | H | CCONH(CH$_2$)$_2$NMe$_2$ | CH | 0.0646 |
| 1 | H | (6) | H | N | CH | 0.39 |
| 1 | H | (5) | H | CCH$_2$—N(morpholine) | CH | 6.57 |
| 1 | H | (5) | 4-pyridyl-CO— | CH | CH | 0.871 |
| 1 | H | (5) | 3-pyridyl-CO— | CH | CH | 0.405 |
| 1 | H | (5) | pyridyl | CH | CH | 0.8 |
| 1 | MeO | (6) | H | tetrahydropyridyl-NH | | 0.242 |
| 1 | Cl | (5) | H | CH | CCH$_3$ | 0.489 |
| 1 | H | (5) | Et$_2$N(CH$_2$)$_3$— | CH | CH | 0.474 |
| 1 | H | (5) | H | tetrahydropyridyl-NH | | 0.33 |
| 1 | H | (6) | H | tetrahydropyridyl-NH | | 0.243 |
| 2 | MeO | (5) | Et$_2$N(CH$_2$)$_2$— | CH | CH | 0.184 |
| 1 | Cl | (5) | H | CH | CCH$_3$ | (43% at 0.2 $\mu$M) |

Several other compounds of the invention were also tested. A compound of formula (3)—i.e., where the carboximide is in the 6-position, $R^1$ is of formula (5), $R^3$ is H, $R^2$ is H, $Z^1$ is CCOCF$_3$ and $Z^2$ is CH showed 41% inhibition at 1 μM. Similarly, a compound where $R^1$ is of formula (5) and substituted at the 6-position of the indole, $R^2$ is

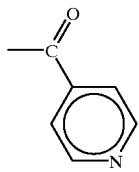

and both $Z^1$ and $Z^2$ are CH, showed an IC$_{50}$ of 0.505 μM.

Two compounds where $R^1$ is of the formula:

(7)

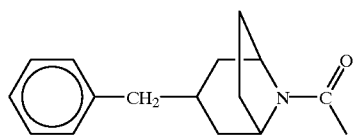

were also tested. In one, of formula (2) wherein $R^3$ is MeO, $R^2$ is H and both $Z^1$ and $Z^2$ are CH, gave 63% inhibition at 0.2 μM; in the other case, which is of formula (3) wherein $R^3$ is H, $R^2$ is H, $Z^1$ is N and $Z^2$ is CH, the IC$_{50}$ was 2.15 μM. Finally, one compound was tested wherein $R^1$ was of the formula:

(8)

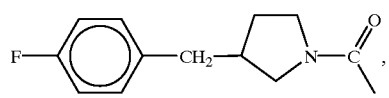

and wherein the invention compound is of formula (3) wherein $R^3$ is H, $R^2$ is H, and both $Z^1$ and $Z^2$ are CH, gave 51% inhibition at 1 μM.

What is claimed is:

1. A compound of the formula:

(1)

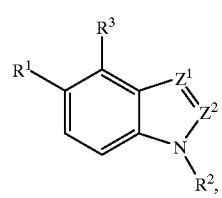

(2)

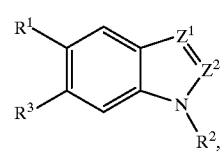

-continued (3)

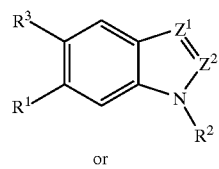

or (4)

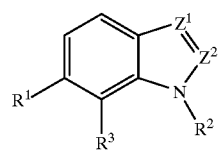

and the pharmaceutically acceptable salts thereof,
wherein each of $Z^1$ and $Z^2$ is independently $CR^4$ or N;
where each $R^4$ is independently selected from H and alkyl (1–6C);
wherein said alkyl optionally includes one or more heteroatoms selected from O, S and N, and wherein said alkyl is optionally substituted by one or more substituents selected from halo, OR, SR, NR$_2$, RCO, COOR, CONR$_2$, OOCR, NROCR, CN, =O, a 5 or 6 membered saturated carbocyclic ring or heterocyclic ring containing 1–2 N, and a 6-membered aromatic ring optionally containing 1–2 N heteroatoms, wherein R in the foregoing optional substituents is H or alkyl (1–6C);
$R^1$ is

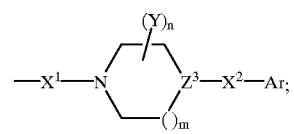

wherein
$X^1$ is CO, SO, CHOH or SO$_2$;
m is 1;
Y is optionally substituted alkyl, optionally substituted aryl, or optionally substituted arylalkyl;
n is 0, 1 or 2;
$Z^3$ is N;
$X^2$ is CH or CH$_2$; and
Ar consists of one or two phenyl moieties directly coupled to $X^2$, said one or two phenyl moieties being optionally substituted by a substituent selected from halo, nitro, alkyl (1–6C), alkenyl (1–6C), CN, CF$_3$, RCO, COOR, CONR$_2$, NR$_2$, OR, SR, OOCR, NROCR, (wherein R in the foregoing is H or 1–6C alkyl), and phenyl, itself optionally substituted by the foregoing substituents;
$R^2$ is selected from H, and alkyl (1–6C);
wherein said alkyl optionally includes one or more heteroatoms which are selected from O, S and N, and wherein said alkyl is optionally substituted by one or more substituents selected from halo, OR, SR, NR$_2$, RCO, COOR, CONR$_2$, OOCR, NROCR, (where R in the foregoing is H or 1–6C alkyl) CN =O, a 5 or 6 membered saturated carbocyclic ring or heterocyclic ring containing 1–2 N, and a 6-membered aromatic ring optionally containing 1–2 N heteroatoms;
with the proviso that if $Z^1$ and $Z^2$ are both CH, $R^2$ is other than H R³ is H, halo, NO₂, alkyl (1–6C), alkenyl (1–6C), CN, OR, SR, NR₂, RCO, COOR, CONR₂, OOCR, or NROCR where R is H or alkyl (1–6C).

2. The compound of claim 1 wherein n is 1 or 2.
3. The compound of claim 1 wherein Z¹ is CR⁴ where R⁴ is not H, and Z² is CH.
4. The compound of claim 3 wherein X¹ is CO.
5. The compound of claim 4 which is of formula (1) or (2).
6. The compound of claim 5 wherein R³ is not H.
7. The compound of claim 5 wherein Ar is phenyl optionally substituted with 1, 2, or 3 halo or up to two OR.
8. The compound of claim 1 which is selected from the group consisting of 4-(2,6-difluorobenzyl)-piperazinyl-benzimidazole-5-carboxamide;
4-(2,3-difluorobenzyl)-piperazinyl-benzimidazole-5-carboxamide;
4-(3,5-difluorobenzyl)-piperazinyl-benzimidazole-5-carboxamide;
4-(3-chlorobenzyl)-piperazinyl-benzimidazole-5-carboxamide;
4-(4-carboxymethyl benzyl)-piperazinyl-benzimidazole-5-carboxamide;
4-(4-methoxybenzyl)-piperazinyl-benzimidazole-5-carboxamide;
4-(4-trifluoromethoxybenzyl)-piperazinyl-benzimidazole-5-carboxamide;
4-(4-methylbenzyl)-piperazinyl-benzimidazole-5arboxamide;
4-(2,4-dichlorobenzoyl)-piperazinyl-benzimidazole-5-carboxamide;
4-(3,4-dichlorobenzoylm)piperazinyl-benzimidazole-5-carboxamnide;
4-[trans-3-(trifluoromethyl)-cinnamoyl]-piperazinyl-benzimidazole-5-carboxmide;
4-(4-chlorobenzoyl)-piperazinyl-benzimidazole-5-carboxamide;
4-benzomethylbenzoylpiperazyl-benzimidazole-5-carboxamide;
4-(2-trifluoromethylbenzoyl)-piperazinyl-benzimidazole-5-carboxamide;
4-(4-methxybenzoyl)-piperazinyl-benzimidazole-5-carboxamide;
4-(3,4-dichlorophenyl)-piperazinyl-benzimnidazole-5-carboxamide;
4-(4-chlorobenzhydryl)-piperazinyl-benzimidazole-5-carboxamide;
4-trans-1-cinnamyl piperazinyl-benzimidazole-5-carboxamide;
4-(4-chlorophenyl)-piperazinyl-benzimidazole-5-carboxamide;
4-[bis(4-fluorophenyl)-methyl]-piperazinyl-benzimidazole-5-carboxamide;
4-(4-chlorobenzyl)-piperazinyl-benzimidazole-5-carboxamide;
4-(2-chlorobenzyl)-piperazinyl-benzimidazole-5-carboxamide;
4-benzylpiperazinyl-benzinudazole-5-carboxamnide;
4-(4-methylthiobenzyl)-piperazinyl-benzimidazole-5-carboxamide;
4-(3,4,5-trimethoxybenzyl)-piperazinyl-benzimidazole-5-carboxamide;
4-(2-naphthylmethyl)-piperazinyl-benzimidazole-5-carboxamide;
4-(4-diethylaminobenzyl)-piperazinyl-benzimidazole-5-carboxamide;
4-(biphenylmethyl)-piperazinyl-benzimidazole-5-carboxamide;
4-(4-phenoxybenzyl)-piperazinyl-benzimidazole-5-carboxamide;
4-(4-quinolinylmethyl)-piperazinyl-benzimidazole-5-carboxamide;
4-(4-chlorobenzyl)-piperazinyl-1-(2-propyl)-indole-5-carboxamide;
4-(3-chlorobenzyl)-piperazinyl-benzimidazole-5-carboxamide;
4-(3-chlorobenzyl)-piperazinyl-N-(2-propyl)-benzimidazole-5-carboxamide;
4-(3-chlorobenzyl)-piperazinyl-N-(2-propyl)-benzimidazole-6-carboxamide;
4-(3-chlorobenzyl)-piperazinyl-N-methyl-benzimidazole-5-carboxamide;
4-(3-chlorobenzyl)-piperazinyl-N-methyl-benzimidazole-6-carboxamide;
4-(3-chlorobenzyl)-piperazinyl-N-ethyl-benzimidazole-5-carboxamide; and
4-(3-chlorobenzyl)-piperazinyl-N-ethyl-benzimidazole-6-carboxamide.

9. A compound of the formula:

(1)

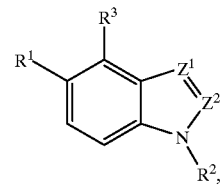

(2)

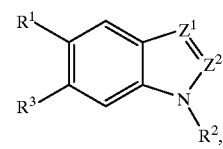

(3)

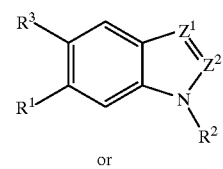

or (4)

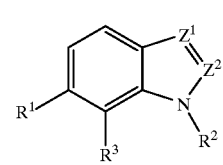

and the pharmaceutically acceptable salts thereof,
wherein each of Z¹ and Z² is independently CR⁴ or N;
where each R⁴ is independently selected from H and alkyl (1–6C);
wherein said alkyl optionally includes one or more heteroatoms selected from O, S and N, and wherein said alkyl is optionally substituted by one or more substituents selected from halo, OR, SR, $NR_2$, RCO, COOR, $CONR_2$, OOCR, NROCR, CN, =O, a 5 or 6 membered saturated carbocyclic ring or heterocyclic ring containing 1–2 N, and a 6-membered aromatic ring optionally containing 1–2 N heteroatoms wherein R in the foregoing optional substituents is H or alkyl (1–6C);

$R^1$ is

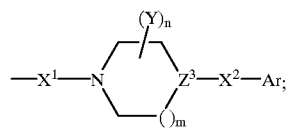

wherein
$X^1$ is CO, $CH_2$, CHOH, SO, or $SO_2$;
m is 1;
Y is optionally substituted alkyl, optionally substituted aryl, or optionally substituted arylalkyl;
n is 0, 1 or 2;
$Z^3$ is N;
$X^2$ is $CH_2$; and
Ar consists of a phenyl moiety directly coupled to $X^2$, said phenyl moiety being optionally substituted by a substituent selected from halo, nitro, alkyl (1–6C), alkenyl (1–6C), CN, $CF_3$, RCO, COOR, $CONR_2$, $NR_2$, OR, SR, OOCR, NROCR (wherein R in the foregoing is H or 1–6C alkyl) and phenyl, itself optionally substituted by the foregoing substituents;
$R^2$ is selected from H and alkyl (1–6C);
wherein sad alkyl optionally includes one or more heteroatoms which are selected from O, S and N, and wherein said alkyl is optionally substituted by one or more substituents selected from halo, OR, SR, $NR_2$, RCO, COOR, $CONR_2$, OOCR, NROCR (where R in the foregoing is H or 1–6C alkyl), CN, =O, a 5 or 6 membered saturated carbocyclic ring or heterocyclic ring containing 1–2 N, and a 6-membered aromaficring optionally containing 1–2 N heteroatoms;
with the proviso that when $Z^1$ and $Z^2$ are CH, $R^2$ is not H;
$R^3$ is H, halo, $NO_2$, alkyl (1–6C), alkenyl (1–6C), CN, OR, SR, $NR_2$, RCO, COOR, $CONR_2$, OOCR, or NROCR where R is H or alkyl (1–6C).

10. A compound of the formula:

(1)
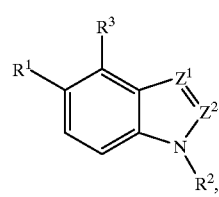

(2)
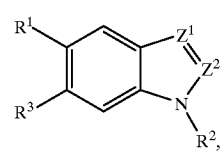

-continued (3)
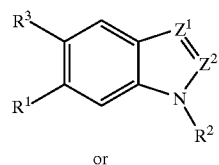

or (4)
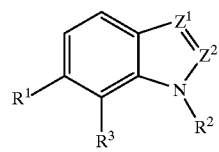

and the pharmaceutically acceptable salts thereof,
wherein each of $Z^1$ and $Z^2$ is $CR^4$;
where each $R^4$ is independently selected from H and alkyl (1–6C);
wherein said alkyl may optionally includes one or more heteroatoms selected from O, S and N and wherein said alkyl is optionally substituted by one or more substituents selected from halo, OR, SR, $NR_2$, RCO, COOR, $CONR_2$, OOCR, NROCR (where R in the foregoing is H or 1–6C alkyl), CN, =O, a 5 or 6 membered saturated carbocyclic ring or heterocyclic ring containing 1–2 N and a 6membered aromatic ring optionally containing 1–2 N heteroatoms;

$R^1$ is

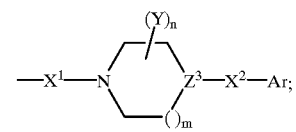

wherein
$X^1$ is CO, SO, CHOH, $SO_2$ or $CH_2$;
m is 1;
Y is optionally substituted alkyl, optionally substituted aryl, or optionally substituted arylalkyl;
n is 1 or 2;
$Z^3$ is N;
$X^2$ is CH or $CH_2$; and
Ar consists of one or two phenyl moieties directly coupled to $X^2$, said Ar being optionally substituted by at least one member selected from the group consisting of halo, nitro, alkyl (1–6C), alkenyl (1–6C), CN, $CF_3$, RCO, COOR, $CONR_2$, $NR_2$, OR, SR, OOCR, NROCR (wherein R in the foregoing is H or alkyl 1–6C), and phenyl, itself optionally substituted by the foregoing substituents;
$R^2$ is selected from H and alkyl (1–6C);
wherein said alkyl optionally includes one or more heteroatoms selected from O, S and N, and wherein said alkyl is optionally substituted by one or more substituents selected from the group consisting of halo, OR, SR, $NR_2$, RCO, COOR, $CONR_2$, OOCR, and NROCR (wherein R in the foregoing is H or 1–6C alkyl), CN, =O, a 5 or 6 membered saturated carbocyclic ring or heterocyclic ring containing 1–2 N, and a 6-membered aromatic ring optionally containing 1–2 N heteroatoms; and
$R^3$ is selected from the group consisting of H, halo, $NO_2$, alkyl (1–6C), alkenyl (1–6C), CN, OR, SR, NR$_2$, RCO, COOR, CONR$_2$, OOCR, and NROCR where R is H or alkyl (1–6C).

11. A compound of the formula:

(1) 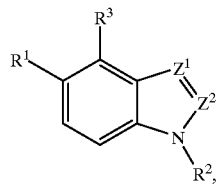

(2) 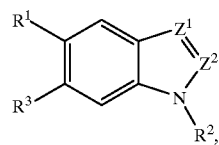

(3) 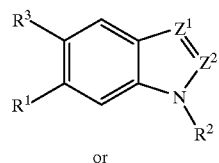

or (4) 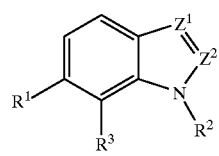

and the pharmaceutically acceptable salts thereof,
wherein Z$^1$ is CR$^{4'}$ and Z$^2$ is CH;
where each R$^{4'}$ is alkyl (1–6C);
wherein said alkyl optionally includes one or more heteroatoms selected from O, S and N and wherein said alkyl is optionally substituted by one or more substituent selected from halo, OR, SR, NR$_2$, RCO, COOR, CONR$_2$, OOCR, NROCR (wherein R in the foregoing is H or 1–6C alkyl), CN, =O, a 5 or 6 membered saturated carbocyclic ring or heterocyclic ring containing 1–2 N, and a 6-membered aromatic ring optionally containing 1–2 N heteroatoms;

R$^1$ is

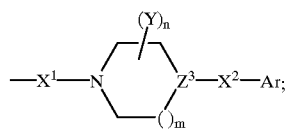

wherein
X$^1$ is CO, SO, CHOH, SO$_2$ or CH$_2$;
m is 1;
Y is optionally substituted alkyl, optionally substituted aryl, or optionally substituted arylalkyl;
n is 0, 1 or 2;
Z$^3$ is N;
X$^2$ is CH or CH$_2$; and
Ar consists of one or two phenyl moieties directly coupled to X$^2$, said Ar being optionally substituted by at least one member selected from the group consisting of halo, nitro, alkyl (1–6C), alkenyl (1–6C), CN, CF$_3$, RCO, COOR, CONR$_2$, NR$_2$, OR, SR, OOCR, NROCR (wherein R in the foregoing is H or alkyl (1–6C), and phenyl, itself optionally substituted by the foregoing substituents;

R$^2$ is selected from H and alkyl (1–6C);
wherein said alkyl optionally includes one or more heteroatoms selected from O, S and N, and wherein said alkyl is optionally substituted by one or more substituents selected from the group consisting of halo, OR, SR, NR$_2$, RCO, COOR, CONR$_2$, OOCR, and NROCR (wherein R in the foregoing is H or 1–6C alkyl), CN, =O, a 5 or 6 membered saturated carbocyclic ring or heterocyclic ring containing 1–2 N, and a 6-membered aromatic ring optionally containing 1–2 N heteroatoms;

R$^3$ is selected from the group consisting of H, halo, NO$_2$, alkyl (1–6C), alkenyl (1–6C), CN, OR, SR, NR$_2$, RCO, COOR, CONR$_2$, OOCR, and NROCR where R is H or alkyl (1–6C).

12. A method for treating inflammatory conditions, which method comprises administering to a human or animal subject in need of such treatment a compound of claim 1, 9, 10 or 11 or a pharmaceutical composition thereof at a dosage range of 0.001–100 mg/kg total body weight thus ameliorating said inflammatory condition.

\* \* \* \* \*

UNITED STATES PATENT AND TRADEMARK OFFICE
CERTIFICATE OF CORRECTION

PATENT NO.    : 6,340,685 B1
DATED         : January 22, 2002
INVENTOR(S)   : Babu J. Mavunkel et al.

It is certified that error appears in the above-identified patent and that said Letters Patent is hereby corrected as shown below:

<u>Column 45,</u>
Line 4, should be corrected to read:
  2.  A compound of the formula:

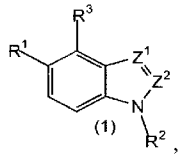
(1)

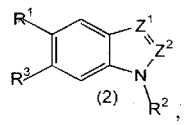
(2)

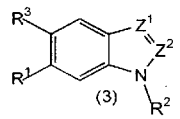
(3)

or

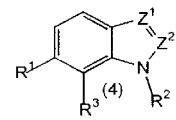
(4)

and the pharmaceutically acceptable salts thereof, wherein each of $Z^1$ and $Z^2$ is independently $CR^4$ or N;

where each $R^4$ is independently selected from H, and alkyl (1-6C);
wherein said alkyl optionally includes one or more heteroatoms selected from O, S and N, and wherein said alkyl is optionally substituted by one or more substituents selected from halo, OR, SR, $NR_2$, RCO, COOR, $CONR_2$, OOCR, NROCR, CN, =O, a 5 or 6 membered saturated carbocyclic ring or heterocyclic ring containing 1-2 N, and a 6-membered aromatic ring optionally containing 1-2 N heteroatoms, wherein R in the foregoing optional substituents is H or alkyl (1-6C);

$R^1$ is

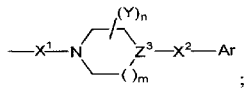

;

wherein
$X^1$ is CO, $CH_2$, CHOH, SO, or $SO_2$;
m is 1;
Y is optionally substituted alkyl, optionally substituted aryl, or optionally substituted arylalkyl;
n is 0, 1 or 2;
$Z^3$ is N;
$X^2$ is $CH_2$; and
Ar consists of a phenyl moiety directly coupled to $X^2$, said phenyl moiety being optionally substituted by a substituent selected from halo, nitro, alkyl (1-6C), alkenyl (1-6C), CN, $CF_3$, RCO, COOR, $CONR_2$, $NR_2$, OR, SR, OOCR, NROCR (wherein R in the foregoing is H or 1-6C alkyl), and phenyl, itself optionally substituted by the foregoing substituents;
$R^2$ is selected from and alkyl (1-6C);
wherein said alkyl optionally includes one or more heteroatoms which are selected from O, S and N, and wherein said alkyl is optionally substituted by one or more substituents selected from halo, OR, SR, $NR_2$, RCO, COOR, $CONR_2$, OOCR, NROCR, (where

UNITED STATES PATENT AND TRADEMARK OFFICE
CERTIFICATE OF CORRECTION

PATENT NO.    : 6,340,685 B1
DATED         : January 22, 2002
INVENTOR(S)   : Babu J. Mavunkel et al.

It is certified that error appears in the above-identified patent and that said Letters Patent is hereby corrected as shown below:

R in the foregoing is H or 1-6C alkyl), CN, =O, a 5 or 6 membered saturated carbocyclic ring or heterocyclic ring containing 1-2 N, and a 6-membered aromatic ring optionally containing 1-2 N heteroatoms;

with the proviso that when $Z^1$ and $Z^2$ are CH, $R^2$ is not H;

$R^3$ is H, halo, $NO_2$, alkyl (1-6C), alkenyl (1-6C), CN, OR, SR, $NR_2$, RCO, COOR, $CONR_2$, OOCR, or NROCR where R is H or alkyl (1-6C).

<u>Column 45 cont'd,</u>
Line 4, should be corrected to read:

3.      The compound of claim 1 or 2 wherein n is 1 or 2.

Line 5, should be corrected to read:

4.      The compound of claim 1 or 2 wherein $Z^1$ is $CR^4$ where $R^4$ is not H, and $Z^2$ is CH.

Line 7, should be corrected to read:

5.      The compound of claim 4 wherein $X^1$ is CO.

Line 8, should be corrected to read:

6.      The compound of claim 5 which is of formula (1) or (2).

Line 9, should be corrected to read:

7.      The compound of claim 6 wherein $R^3$ is not H.

Line 10, should be corrected to read:

8.      The compound of claim 6 wherein Ar is phenyl optionally substituted with 1,2 or 3 halo or up to two OR.

UNITED STATES PATENT AND TRADEMARK OFFICE
CERTIFICATE OF CORRECTION

PATENT NO. : 6,340,685 B1
DATED : January 22, 2002
INVENTOR(S) : Babu J. Mavunkel et al.

It is certified that error appears in the above-identified patent and that said Letters Patent is hereby corrected as shown below:

<u>Column 45 cont'd,</u>
Line 12, should be corrected to read:

9. The compound of claim 1 which is selected from the group consisting of 4-(2,6-difluorobenzyl)-piperazinyl-benzimidazole-5-carboxamide;

4-(2,3-difluorobenzyl)-piperazinyl-benzimidazole-5-carboxamide;

4-(3,5-difluorobenzyl)-piperazinyl-benzimidazole-5-carboxamide;

4-(3-chlorobenzyl)-piperazinyl-benzimidazole-5-carboxamide;

4-(4-carboxymethyl benzyl)-piperazinyl-benzimidazole-5-carboxamide;

4-(4-methoxybenzyl)-piperazinyl-benzimidazole-5-carboxamide;

4-(4-trifluoromethoxybenzyl)-piperazinyl-benzimidazole-5-carboxamide;

4-(4-methylbenzyl)-piperazinyl-benzimidazole-5-carboxamide;

4-(2,4-dichlorobenzoyl)-piperazinyl-benzimidazole-5-carboxamide;

4-(3,4-dichlorobenzoyl)-piperazinyl-benzimidazole-5-carboxamide;

4-[trans-3-(trifluoromethyl)-cinnamoyl]-piperazinyl-benzimidazole-5-carboxamide;

4-(4-chlorobenzoyl)-piperazinyl-benzimidazole-5-carboxamide;

4-benzoylpiperazinyl-benzimidazole-5-carboxamide;

4-(2-trifluoromethylbenzoyl)-piperazinyl-benzimidazole-5-carboxamide;

4-(4-methxybenzoyl)-piperazinyl-benzimidazole-5-carboxamide;

4-(3,4-dichlorophenyl)-piperazinyl-benzimidazole-5-carboxamide;

4-(4-chlorobenzhydryl)-piperazinyl-benzimidazole-5-carboxamide;

4-trans-1-cinnamyl piperazinyl-benzimidazole-5-carboxamide;

4-(4-chlorophenyl)-piperazinyl-benzimidazole-5-carboxamide;

4-[bis(4-fluorophenyl)-methyl]-piperazinyl-benzimidazole-5-carboxamide;

4-(4-chlorobenzyl)-piperazinyl-benzimidazole-5-carboxamide;

4-(2-chlorobenzyl)-piperazinyl-benzimidazole-5-carboxamide;

4-benzylpiperazinyl-benzimidazole-5-carboxamide;

4-(4-methylthiobenzyl)-piperazinyl-benzimidazole-5-carboxamide;

4-(3,4,5-trimethoxybenzyl)-piperazinyl-benzimidazole-5-carboxamide;

4-(2-naphthylmethyl)-piperazinyl-benzimidazole-5-carboxamide;

UNITED STATES PATENT AND TRADEMARK OFFICE
CERTIFICATE OF CORRECTION

PATENT NO. : 6,340,685 B1
DATED : January 22, 2002
INVENTOR(S) : Babu J. Mavunkel et al.

It is certified that error appears in the above-identified patent and that said Letters Patent is hereby corrected as shown below:

4-(4-diethylaminobenzyl)-piperazinyl-benzimidazole-5-carboxamide;
    4-(biphenylmethyl)-piperazinyl-benzimidazole-5-carboxamide;
    4-(4-phenoxybenzyl)-piperazinyl-benzimidazole-5-carboxamide;
    4-(4-quinolinylmethyl)-piperazinyl-benzimidazole-5-carboxamide;
    4-(4-chlorobenzyl)-piperazinyl-1-(2-propyl)-indole-5-carboxamide;
    4-(3-chlorobenzyl)-piperazinyl-benzimidazole-5-carboxamide;
    4-(3-chlorobenzyl)-piperazinyl-N-(2-propyl)-benzimidazole-5-carboxamide;
    4-(3-chlorobenzyl)-piperazinyl-N-(2-propyl)-benzimidazole-6-carboxamide;
    4-(3-chlorobenzyl)-piperazinyl-N-methyl-benzimidazole-5-carboxamide;
    4-(3-chlorobenzyl)-piperazinyl-N-methyl-benzimidazole-6-carboxamide;
    4-(3-chlorobenzyl)-piperazinyl-N-ethyl-benzimidazole-5-carboxamide; and
    4-(3-chlorobenzyl)-piperazinyl-N-ethyl-benzimidazole-6-carboxamide.

Column 50,
Line 42, should be corrected to read:

12. A method for treating inflammatory conditions, which method comprises administering to a human or animal subject in need of such treatment a compound of claim 1, 2, 10 or 11 or a pharmaceutical composition thereof at a dosage range of 0.001-100 mg/kg total body weight thus ameliorating said inflammatory condition.

Signed and Sealed this

Third Day of June, 2003

JAMES E. ROGAN
*Director of the United States Patent and Trademark Office*